US012594127B2

(12) United States Patent (10) Patent No.: US 12,594,127 B2
Bette et al. (45) Date of Patent: *Apr. 7, 2026

(54) SURGICAL SYSTEM WITH NAVIGATION

(71) Applicants: SpineGuard, Vincennes (FR);
Sorbonne Universite, Paris (FR);
**INSERM (Institut National de la
Sante et de la Recherche Medicale)**,
Paris (FR); **Centre National de la
Recherche Scientifique—CNRS**, Paris
(FR)

(72) Inventors: Stéphane Bette, Vincennes (FR);
Maurice Bourlion, Rive de Gier (FR);
Thibault Chandanson, Vincennes (FR)

(73) Assignees: SpineGuard, Vincennes (FR);
Sorbonne Universite, Paris (FR);
**INSERM (Institut National de la
Sante et de la Recherche Medicale)**,
Paris (FR); **Centre National de la
Recherche Scientifique-CNRS**, Paris
(FR)

( * ) Notice: Subject to any disclaimer, the term of this
patent is extended or adjusted under 35
U.S.C. 154(b) by 878 days.

This patent is subject to a terminal dis-
claimer.

(21) Appl. No.: 17/659,167

(22) Filed: Apr. 13, 2022

(65) Prior Publication Data

US 2022/0233250 A1 Jul. 28, 2022

Related U.S. Application Data

(63) Continuation-in-part of application No. 17/334,566,
filed on May 28, 2021, now Pat. No. 11,344,372,
(Continued)

(30) Foreign Application Priority Data

Oct. 24, 2017 (FR) ...................................... 17 60056

(51) Int. Cl.
*A61B 17/16* (2006.01)
*A61B 5/053* (2021.01)
(Continued)

(52) U.S. Cl.
CPC .............. *A61B 34/20* (2016.02); *A61B 5/053*
(2013.01); *A61B 5/150809* (2013.01);
(Continued)

(58) Field of Classification Search
CPC .................................................... A61B 34/20
See application file for complete search history.

(56) References Cited

U.S. PATENT DOCUMENTS 6,470,207 B1 10/2002 Simon et al.
6,635,062 B2* 10/2003 Ray, III ............. A61B 17/1671
606/279

(Continued)

FOREIGN PATENT DOCUMENTS

CN 103948412 A 7/2014
EP 1474046 A1 11/2004
(Continued)

OTHER PUBLICATIONS

International Search Report & Written Opinion dated Dec. 15, 2022
in Int'l PCT Patent Appl. No. PCT/IB2022/059201 (0410).
(Continued)

*Primary Examiner* — Christian A Sevilla
(74) *Attorney, Agent, or Firm* — GREENBERG
TRAURIG, LLP; Christopher C. Bolten; Albert K. Heng

(57) ABSTRACT

Systems, instruments, and methods are provided verifying
the surgery is being performed in accordance with a surgical
plan, wherein a surgical tool having a sensor outputs a data
signal that enables the trajectory of the surgical tool to be
displayed as an overlay on an image of an anatomical
portion of a patient and a visual or audible signal that
(Continued)

confirms the surgical tool is penetrating the anatomical portion in accordance with the surgical plan and/or that issues an alert indicating that the surgical tool is not being inserted into the anatomical portion according to the surgical plan.

20 Claims, 13 Drawing Sheets

Related U.S. Application Data which is a continuation-in-part of application No. 16/757,937, filed as application No. PCT/FR2018/052640 on Oct. 24, 2018, now Pat. No. 11,399,902.

(51) Int. Cl.

| | | |
|---|---|---|
| *A61B 5/15* | (2006.01) | |
| *A61B 17/17* | (2006.01) | |
| *A61B 34/10* | (2016.01) | |
| *A61B 34/20* | (2016.01) | |
| *A61B 34/30* | (2016.01) | |
| *A61B 17/00* | (2006.01) | |
| *A61B 34/00* | (2016.01) | |

(52) U.S. Cl.
CPC ...... *A61B 17/1615* (2013.01); *A61B 17/1703* (2013.01); *A61B 34/10* (2016.02); *A61B 2017/00199* (2013.01); *A61B 2034/107* (2016.02); *A61B 2034/2055* (2016.02); *A61B 2034/252* (2016.02); *A61B 2034/254* (2016.02)

(56) References Cited

U.S. PATENT DOCUMENTS

| | | | | |
|---|---|---|---|---|
| 6,796,985 | B2 | 9/2004 | Bolger et al. | |
| 7,580,743 | B2 | 8/2009 | Bourlion et al. | |
| 8,092,457 | B2 * | 1/2012 | Oettinger | A61B 17/1626 |
| | | | | 606/80 |
| 8,361,152 | B2 * | 1/2013 | McCormack | A61B 17/1659 |
| | | | | 623/17.15 |
| 8,419,746 | B2 | 4/2013 | Bourlion et al. | |
| 8,486,119 | B2 | 7/2013 | Bourlion | |
| 8,634,897 | B2 | 1/2014 | Simon et al. | |
| 8,795,285 | B2 * | 8/2014 | Kwon | A61B 17/1757 |
| | | | | 606/99 |
| 9,066,751 | B2 | 6/2015 | Sasso | |
| 9,204,830 | B2 | 12/2015 | Zand et al. | |
| 9,538,935 | B2 | 1/2017 | Bourlion et al. | |
| 9,901,283 | B2 | 2/2018 | Bourlion et al. | |
| 10,064,630 | B2 | 9/2018 | Forman et al. | |
| 10,149,729 | B2 | 12/2018 | Smaby et al. | |
| 10,624,572 | B2 | 4/2020 | Bourlion et al. | |
| 11,344,372 | B2 | 5/2022 | Bourlion et al. | |
| 11,399,902 | B2 | 8/2022 | Bourlion et al. | |
| 2005/0119660 | A1 | 6/2005 | Bourlion et al. | |
| 2006/0241628 | A1 | 10/2006 | Parak | |
| 2007/0236514 | A1 * | 10/2007 | Agusanto | G06T 19/006 |
| | | | | 345/646 |
| 2009/0157059 | A1 | 6/2009 | Allen et al. | |
| 2010/0024981 | A1 | 2/2010 | Wallace et al. | |
| 2011/0015649 | A1 | 1/2011 | Anvari et al. | |
| 2012/0046668 | A1 | 2/2012 | Gantes | |
| 2012/0296213 | A1 | 11/2012 | Mauldin, Jr. et al. | |
| 2013/0085413 | A1 | 4/2013 | Tsamir et al. | |
| 2013/0085505 | A1 | 4/2013 | Markey et al. | |
| 2014/0094808 | A1 | 4/2014 | Herndon | |
| 2014/0276002 | A1 | 9/2014 | West et al. | |
| 2014/0276950 | A1 | 9/2014 | Smaby et al. | |
| 2014/0324044 | A1 | 10/2014 | Haufe et al. | |
| 2015/0366624 | A1 | 12/2015 | Kostrzewski et al. | |
| 2016/0074123 | A1 | 3/2016 | Bly et al. | |
| 2016/0302871 | A1 | 10/2016 | Gregerson et al. | |
| 2017/0007199 | A1 | 1/2017 | Bourlion et al. | |
| 2017/0056116 | A1 * | 3/2017 | Kostrzewski | B25J 19/06 |
| 2017/0360493 | A1 | 12/2017 | Zucker et al. | |
| 2018/0042514 | A1 | 2/2018 | Verard et al. | |
| 2018/0098714 | A1 | 4/2018 | Bourlion et al. | |
| 2018/0177556 | A1 | 6/2018 | Noonan | |
| 2019/0175886 | A1 | 6/2019 | Abdelwahed et al. | |
| 2019/0388173 | A1 | 12/2019 | Pak et al. | |
| 2020/0324408 | A1 | 10/2020 | Bourlion et al. | |
| 2020/0337782 | A1 | 10/2020 | Glassman et al. | |
| 2021/0068905 | A1 * | 3/2021 | Quaid | A61F 2/30942 |
| 2021/0282862 | A1 | 9/2021 | Bourlion et al. | |
| 2022/0104901 | A1 | 4/2022 | Lawrie | |
| 2022/0168048 | A1 | 6/2022 | Shoham et al. | |
| 2022/0175455 | A1 | 6/2022 | Ungi et al. | |
| 2022/0175462 | A1 | 6/2022 | Turgeman et al. | |
| 2022/0218421 | A1 | 7/2022 | Junio et al. | |

FOREIGN PATENT DOCUMENTS

| | | | |
|---|---|---|---|
| EP | 3319539 | A1 | 5/2018 |
| EP | 3525696 | A1 | 8/2019 |
| EP | 3761870 | A1 | 1/2021 |
| EP | 3883491 | A1 | 9/2021 |
| FR | 2795624 | A1 | 1/2001 |
| FR | 3034643 | A1 | 10/2016 |
| JP | 2005-525150 | A | 8/2005 |
| JP | 2016-518878 | A | 6/2016 |
| WO | WO-03068076 | A1 | 8/2003 |
| WO | WO-2014146090 | A1 | 9/2014 |
| WO | WO-2015006296 | A1 | 1/2015 |
| WO | WO-2016043676 | A1 | 3/2016 |
| WO | WO-2016162634 | A1 | 10/2016 |
| WO | WO-2016199152 | A1 | 12/2016 |
| WO | WO-2020000038 | A1 | 1/2020 |
| WO | WO-2020097481 | A1 | 5/2020 |
| WO | WO-2021046247 | A1 | 3/2021 |
| WO | WO-2021111439 | A1 | 6/2021 |
| WO | WO-2022170185 | A1 | 8/2022 |

OTHER PUBLICATIONS

International Search Report & Written Opinion dated Aug. 31, 2022 in Int'l PCT Patent Appl. Serial No. PCT/EP2022/061868 (0310). Int'l Search Report & Written Opinion dated Jan. 7, 2019 in Int'l PCT Patent Appl. Serial No. PCT/FR2018/052640.

* cited by examiner

200 ⟍

SURGICAL SYSTEM WITH NAVIGATION

REFERENCE TO RELATED APPLICATIONS

This application is a continuation-in-part of U.S. patent application Ser. No. 17/334,566, filed May 28, 2021, which is a continuation-in-part of U.S. patent application Ser. No. 16/757,937, filed Oct. 24, 2018, which is a national stage application of International PCT Patent Application Serial No. PCT/FR2018/052640, filed Oct. 24, 2018, and claims priority to French Patent Application Serial No. FR 17-60056, filed Oct. 24, 2017, the entire contents of each of which are incorporated herein by reference.

I. FIELD OF THE INVENTION

The invention relates to a surgical system in which a trajectory of a working end of a penetrating tool is guided by an impedance sensing system and wherein progress of the working end may be visualized with a navigation system that includes an imaging system.

II. BACKGROUND OF THE INVENTION

Image based surgical techniques have been used to aid physicians in performing a wide variety of delicate surgical procedures. These surgical procedures are used, for example, when patient anatomy obscures visualization of a surgical tool, or when a working end of a surgical tool is difficult to visualize in three dimensions. Surgical procedures in which such concerns frequently arise include, for example, spinal implant placement, alignment of broken bone fragments, and fixation of bone fractures.

Surgical navigation and robotic systems are known that use x-ray or fluoroscopic images to assist a physician in visualizing the location of a working end of a surgical tool within patient anatomy. Such systems repeatedly acquire x-ray or CT images during a surgical procedure, thereby permitting real-time display of a position of the working end of the surgical tool relative to the patient anatomy. Fluoroscopically-based surgical navigation systems also may track a trajectory of the surgical tool and superimpose a representation of the surgical tool onto pre-acquired images of the patient anatomy, without x-rays being taken repeatedly during the surgical procedure. An example of such a system is the Stealth Station® navigation system sold by Medtronic, Inc., which provides a surgeon with CT-imaging feedback of the position and trajectory of handheld instruments.

Adoption of previously known surgical navigation systems has been limited because the accuracy of such systems may be compromised by a variety of factors. For example, a patient or the surgeon may reposition the patient's body on the surgical table, thereby causing mis-registration of the working end of the surgical tool relative to pre-acquired images. One solution to this problem, to periodically update the fluoroscopic or CT-images during the surgical procedure, disadvantageously subjects the patient and the surgeon to greater exposure to ionizing radiation.

Yet another inherent limitation of previously known navigation systems is the inability to provide a high degree of confidence of the location of the working end of a surgical tool in three-dimensions, based on two-dimensional displayed images. While navigation systems may provide multiple views of the patient's anatomy and the working end, it may be challenging for the surgeon to mentally integrate such views in real time to achieve a high degree of confidence about the location of the working end of the surgical tool.

The foregoing drawbacks may become even more acute where the surgeon is directing a robotic arm to perform the surgery. While robotic systems provide important benefits, such as reducing surgeon fatigue and eliminating transmission of physician muscle tremors during delicate operations, such systems also typically reduce the physician's tactile feel during advancement of the working end, for example, when passing from bone into tissue. This concern is accentuated when working with delicate structures innervated with critical nervous system components, such as the spine, where maintaining high precision is vital to the patient's safety.

Accordingly, it would be desirable to provide systems and methods that improve upon known surgical navigation systems, and which enable a surgeon accurately to confirm the location of the working end of a surgical tool in three-dimensional space. Such improved systems and methods would offer a surgeon a high degree of confidence that a navigation-assisted surgery is being conducted in accordance with pre-operative plans.

It further would be desirable to provide systems and methods that improve real-time registration of a working end of a surgical tool with images displayed on a navigation system and which could alert the surgeon when the working end is approaching a transition in the anatomy.

It still further would be desirable to provide systems and methods for use with a navigation system that not only alerts a surgeon when the working end is approaching a transition in the anatomy, but also provides a revised trajectory for the tool or surgeon to avoid the anatomical transition.

III. SUMMARY OF THE INVENTION

In accordance with the principles of the present invention, systems and methods are provided that improve upon known surgical navigation systems, by enabling a surgeon accurately to confirm the location of the working end of a surgical tool in three-dimensional space. The inventive systems and methods permit a surgeon to achieve a high degree of confidence that a navigation-assisted surgery is being conducted according to pre-operative plans.

Further in accordance with invention, systems and methods are provided that improve real-time registration of a working end of a surgical tool with images displayed on a navigation system. The inventive systems and methods may alert a surgeon when the working end is approaching a transition in the anatomy that is being traversed by the working end. Further, the inventive systems and methods may suggest to the surgeon, or directly implement via feedback to the mechanism controlling movement of surgical tool, a revised trajectory for the working end of the surgical tool to avoid the anatomical transition.

In one exemplary embodiment, the inventive medical system includes a robotic arm having a base and a surgical tool having an effector, the robotic arm configured to allow movement of the effector relative to the base, and a control unit connected to the robotic arm and configured to issue a signal that controls movement of the tool and effector relative to the base. In one embodiment, the robotic arm is controlled by the control unit and used by a surgeon to perform at least some of his gestures during a surgical procedure on an anatomical portion. In a preferred embodiment, the medical system includes a navigation system that displays an overlay of the tool and effector on images of the anatomical portion. The images of the anatomical portion may be pre-acquired or acquired in real time during the surgical procedure. In a preferred embodiment, the medical system is designed to improve the gesture precision and to prevent damage to particularly sensitive tissues of the anatomical portion.

In an embodiment for use in orthopedic surgery or spine surgery, the medical system may be used to control movement and trajectory of a medical device, e.g., a medical or surgical instrument, tool or implant, relative to boney anatomical structure. The inventive system may reduce the risk of damage caused by inadvertent intrusion into areas of functional tissue, such as nervous system tissue, near the boney structure. The inventive system and methods are particularly advantageous in controlling the movement of the medical device involved in attaching an implant in the pedicle of a vertebra of the spine, in immediate proximity to the functional tissue that include the spinal cord, nerve endings, and vascular structures.

During the surgical procedure, movement of the medical device is generally controlled by a navigation system including a tracking device and a display device. The tracking device may comprise targets of any suitable nature, integral with of affixed to the medical device, and one or more target detection members, such as optical cameras. The control unit thus may detect a position of the medical device within a reference frame, determined by the tracking device, and display it on the display device superimposed on a representation of the anatomical portion. In accordance with one aspect of the invention, the medical system includes a device designed to penetrate an anatomical portion composed of different mediums having different electrical characteristics, which characteristics vary as a function of the capacities of the mediums to conduct electric current. Further in accordance with the inventive principles, the device is configured to sense the different electrical characteristics of the different mediums, and emit a warning signal when a transition in the electrical characteristics is sensed. The control unit controlling movement of the robotic arm, responsive to the detection of an impending transition in electrical characteristics, may cease movement of the device, or revise the trajectory of the device, within the anatomical portion to avoid the transition.

The present invention also relates to a method of verifying a trajectory of a surgical tool during a procedure. The method includes receiving one or more images of an anatomical portion of a patient and executing a surgical plan to insert a medical device into the anatomical portion, during which sensor data is collected from one or more sensors embodied in the medical device as it is being inserted into the anatomical portion. The method further includes determining whether the sensor data corresponds to the surgical plan; and sending, in response to determining that the sensor data does not correspond to the surgical plan, an alert indicating that the surgical tool is not being inserted according to the surgical plan.

In one embodiment, the medical device includes a bipolar electrode sensing arrangement, wherein a body of the medical device extends between a distal end designed to penetrate an anatomical portion and having an external surface, and a proximal end, opposite the distal end. Preferably, the body has at least one first electrode comprising a first contact surface arranged on the external surface at the distal end, configured to contact the anatomical portion, and at least one second electrode having a second contact surface, arranged on the external surface at the distal end, to contact the anatomical portion at a distance from the first contact surface. An electric generator may be connected to the first and second electrodes to apply a voltage between the first and second contact surfaces. A processing device is connected to the electric generator and the first and second electrodes and programmed to determine a measurement parameter related to the electrical characteristic based on a measured electric current between the first and second electrodes, and to emit a warning signal corresponding to the measurement parameter. The control unit is configured to issue a control signal to control movement of the medical device responsive to the warning signal.

The inventive system and method thus makes it possible to control the movement of the surgical tool based on a warning signal representative of the relative positions of the body of the medical device and the anatomical portion. Such control based on the actual position of the body of the medical device relative to the anatomical portion improves the reliability and safety of the medical system. In addition, the inventive system and method may be employed with previously-known navigation systems to improve precision of the representation of the medical device relative to the anatomical portion, for example, resulting from the acquisition of MRI or ultrasound images.

In accordance with another aspect of the invention, a medical system includes a surgical navigation system for verifying a trajectory of a medical device during a procedure. The surgical navigation system includes at least one sensor arrangement attached to the medical device, an imaging system configured to capture images of an anatomical portion of a patient and to transmit the captured images to a control system, and a control system configured to operate the medical device. In some preferred embodiments, the control system is configured to receive the captured images and to execute a surgical plan to insert the medical device into the anatomical portion using a robotic arm. The control system also is configured to receive sensor data collected from the sensor arrangement as the medical device is being inserted into the anatomical portion, to determine whether the data provided by the sensor arrangement corresponds to the surgical plan. If the control system determines that the sensor data does not correspond to the surgical plan, an alert is generated indicating that the medical device is not being inserted according to the surgical plan.

In yet another aspect of the invention, a computer program is provided that includes a non-transitory computer-readable storage medium containing program instructions for verifying a trajectory of a medical device during a surgical procedure, in which the program instructions are executable by at least one processor. The program instructions include receiving a captured image of an anatomical portion of a patient, and executing a surgical plan to insert a medical device into the anatomical portion. Further in accordance with the invention, the program instructions include receiving sensor data collected from a sensor arrangement being inserted into the anatomical portion, the sensor arrangement embodied in or affixed to the medical device. Preferably, the program instructions include determining whether the data generated by the sensor arrangement corresponds to the surgical plan. If it does not, the program instructions include sending an alert indicating that the medical device is not being inserted according to the surgical plan.

IV. BRIEF DESCRIPTION OF THE DRAWINGS

The foregoing and other objects, features and advantages of the invention will be apparent from the following more particular descriptions of exemplary embodiments of the invention as illustrated in the accompanying drawings wherein like reference numbers generally represent like parts of the disclosure.

V. DETAILED DESCRIPTION OF THE INVENTION

The present invention is particularly advantageous for use in the field of orthopedic surgery and spine surgery to assist a surgeon during a surgical procedure placing an implant in one or more vertebrae of a patient's spine. The assistance of the medical system may be partial, controlling only a portion of the surgeon's gestures, complete, controlling the gestures in place of the surgeon, or a combination of the two. The inventive medical system thus enables improving the precision of the gestures and preventing the risk of damage related to unintended intrusion into sensitive functional tissues, such as the spinal cord, nerve endings, and vascular structures. Although the system and methods of the invention are described herein with respect to an application in a vertebra, and more generally in a boney structure, they are not limited to such an application. Instead, the principles of the present invention advantageously may be applied to any anatomical portion comprising different mediums and having an electrical characteristic, such as a conductivity or resistivity, which varies as a function of the capacities of the mediums to conduct an electric current.

Figure 1:
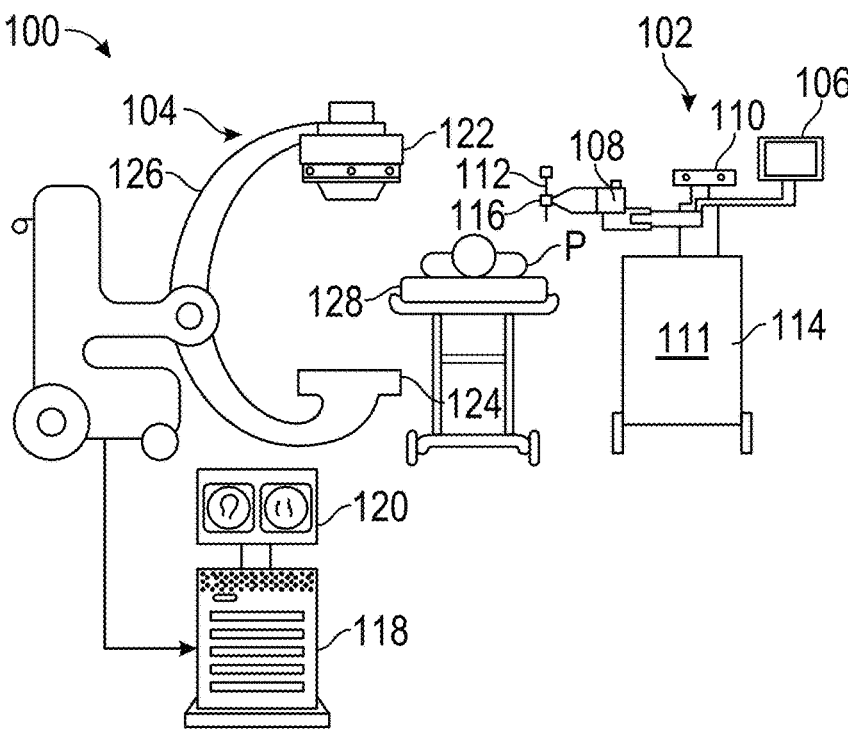
FIG. 1 illustrates an exemplary surgical system constructed in accordance with the principles of the present invention that includes a robotic arm having a medical device, control unit, surgical navigation system, imaging system and display.

Referring now to FIG. 1, an illustrative operating environment for spinal surgical procedures arranged in accordance with the principles of the present invention is described. Operating environment 100 includes precision guidance system 102 and imaging system 104. Operating environment 100 enables a surgeon to generate and display images of a trajectory of a surgical instrument within an anatomy of patient P during a surgical procedure. An exemplary surgical navigation system is described in U.S. Pat. No. 8,634,897 B2, the entirety of which is hereby incorporated by reference. Commercial embodiments of surgical navigation systems include, for example, the FluoroNav®. system, which utilizes the StealthStation® Treatment Guidance Platform, both of which are available from Medtronic Sofamor Danek, Inc. The StealthStation® Treatment Guidance Platform, and in particular the StealthStation® Navigation System, is described in part in the "StealthStation® S8 Spinal Navigation Solution" brochure published by Medtronic, Inc., circa 2019, and in "The Clinical and Economic Benefits of Using StealthStation® Navigation and O-Arm® Imaging Systems for Spine Surgery" brochure published by Medtronic, Inc., circa 2014. Such surgical navigation systems may be used in combination with robotic systems, such as, for example, the Mazor X® Stealth Edition, available from Medtronic, Inc.

Precision guidance system 102 may include monitor 106, robotic 108, camera 110, and control unit 111, which has one or more processors and at least one computer readable medium. The computer may be any programmable electronic device or computing system capable of receiving and sending data and performing computer-readable program instructions on the at least one computer readable medium. The computer-readable program instructions may be instructions to operate a medical system, illustratively described as method 200 in FIG. 6. The one or more processors may be configured to execute program instructions to verify a trajectory of a surgical tool, such as a pedicle access needle, Jamshidi needle, guidewire, or probe 112, during a surgical procedure. Monitor 106, robot 108, and camera 110 each may be pivotably coupled to base 114 of precision guidance system 102. Camera 110 may be an integrated 3D camera with spatial tracking features. Camera 110 may be used to track the movements of robotic arm 108 to enable precision guidance system 102 to control movement instructions for robot 108.

Monitor 106 may include a control panel for a user to interact with in a sterile area of operating environment 100. Monitor 106 may display a surgical plan and/or an actual trajectory of a surgical tool, for example, drill bit 112, within an anatomical portion of patient P. Monitor 106 may be configured to receive and display images from imaging system 104.

Operation of robot 108 is controlled by control unit 111 of precision guidance system 102, which in one embodiment provides movement instructions to robot 108, for example, as determined by a surgeon or in accordance with a surgical plan. Robot 108 may be configured to rotate about one or more axes to perform a surgical procedure. Robot 108 also may include instrument holder 116, configured in a variety of shapes, to secure tools, such as surgical tools, to the distal end of robot 108. For example, instrument holder 116 may be configured to receive and hold a penetrating device, such as a drill bit.

Imaging system 104 illustratively includes workstation 118 having workstation monitor 120, and image receiving section 122 coupled to image generating section 124 via arm 126. Arm 126 has a shape that enables image receiving section 122 and image generating section 124 to be positioned above and below patient P laying on surgical table 128. For example, arm 126 may be configured in a "C" shape such that image generating section 124 is positioned at a bottom distal end of the C-shape arm, and image receiving section 122 is positioned at an upper distal end of the C-shape arm. When imaging system 104 is positioned to take images of patient P, image generating section 124, patient P, and image receiving section 122 are linearly aligned with one another.

Imaging system 104 may be a computed tomography (CT) fluoroscopic image-based surgical navigation system configured to acquire and display CT images and/or x-ray images appropriate for a given surgical procedure. However, it should be understood that imaging system 104 is not limited to use with any particular image guided surgical system. For example, imaging system 104 may acquire images from other modalities than CT fluoroscopic image-based surgical navigation system, including, for example, ultrasound, PET, or magnetic resonance imaging. CT images and/or x-ray images may be collected when patient P is positioned laying on surgical table 128 within arm 126 of imaging system 104, with the images preferably taken at a time prior to initiation of a surgical procedure. Preferably, the images may be taken from two orthogonal directions, such as anterior-posterior (A-P) and lateral, of the anatomical portion of patient P. Imaging system 104 may transmit the acquired images from image receiving section 122 to workstation 118, which may be configured to display the received images via workstation monitor 120. Imaging system 104 also may provide the received images to precision guidance system 102.

Figure 2:
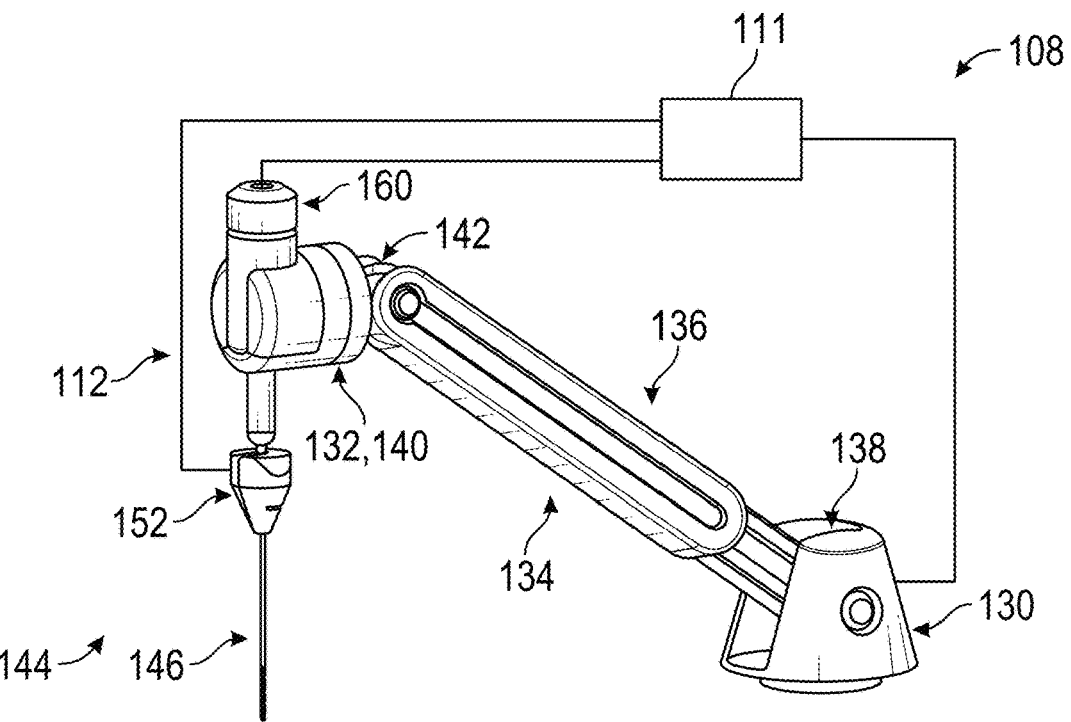
FIG. 2 is a detailed view of an exemplary robotic arm for use in the surgical system depicted in FIG. 1, in which the medical device includes a body suitable for penetrating an anatomical portion having variable electrical characteristics.
Figure 3:
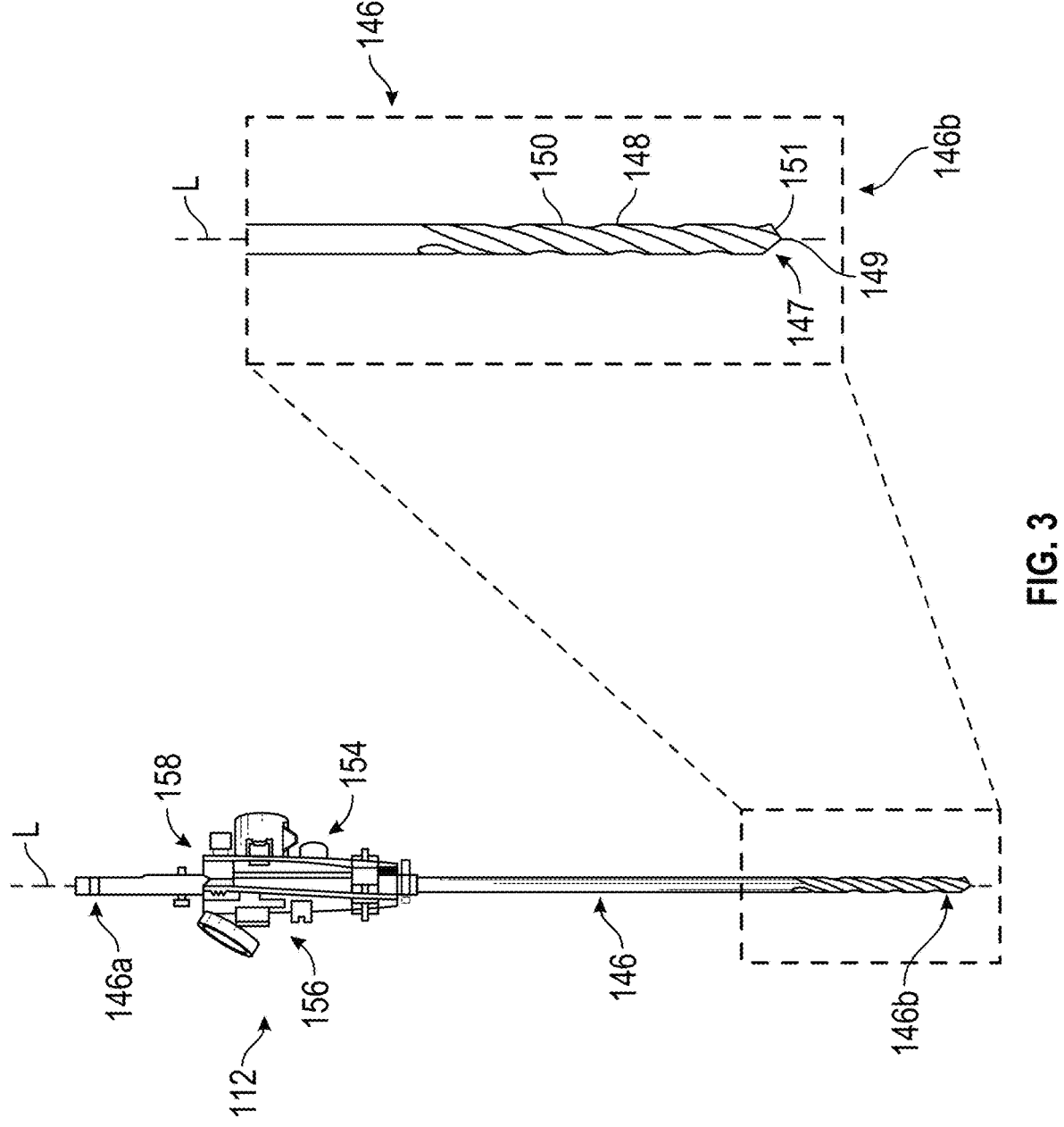
FIG. 3 is a detailed view of the exemplary medical device of FIG. 2.

Referring now to FIG. 2, robot 108 and probe 112 coupled to control unit 111 of FIG. 1 are described in greater detail. Robot 108 includes base 130 and effector 132 arranged, in the embodiment shown, opposite to base 130. Robotic arm 134 is configured to enable movement of effector 132 relative to base 130. In particular, the robotic arm 134 may include several segments linked together by joints. In the embodiment shown, a first segment constitutes base 130 on which a first end of a second segment 136 is mounted by means of joint 138 having an appropriate number of degrees of freedom. A third segment 140 carrying effector 132 is mounted on a second end of second segment 136 by means of a second joint 142, also having an appropriate number of degrees of freedom. At least one of joints 138, 142 is equipped with at least one actuator. As will be apparent from the following description, the actuators of the joints may be reversible, thus allowing relative movement of the segments relative to one another under the effect of an external action exerted on robot 108, e.g., applied by a surgeon on robotic arm 134. At least one of the reversible actuators is controlled by control unit 114.

Medical device or probe 112 is configured to penetrate an anatomical portion, such as a region that includes a vertebra and surrounding tissue. It is important to ensure precise positioning of medical device 112 to avoid damaging, or even worse, passing through, the inner layer of cortical bone delimiting the foramen, or the outer layer, of cortical bone near the nerve endings. Medical device 112 preferably is configured to emit a warning signal that varies as a function of the sensed electrical characteristic when it is moved within an anatomical portion.

Still referring to FIG. 2, medical device 112 illustratively is instrumented drilling device 144, and operates analogously to the hand tool described in U.S. Pat. No. 7,580,743, which is incorporated herein by reference, which device is commercially available from the assignee of the present application under the tradename PediGuard®. Although described in relation to drilling device 144, it is to be understood that the invention is not limited to this specific type of medical device, and may be implemented with other types of medical or surgical tools or instruments, such as a probe, a square tip rongeur, spatula, curette, or tap. Medical device 112 also may constitute an implant to be placed in the anatomical structure, such as a screw, and in particular a pedicle screw.

Drilling device 144 includes drill bit 146 suitable for penetrating the boney structure of a vertebra. Drill bit 146 extends along longitudinal axis L between proximal end 146*a* and distal end 146*b*, forming tip 147 for penetrating boney structure. Drill bit 146 generally has a cylindrical external surface of circular cross-section around longitudinal axis L and is provided with one or more spiral cutting edges near tip 147. The body of drill bit 146 could, however, have any other shape, in particular cylindrical with a polygonal or other cross-section.

Drill bit 146 comprises first electrode 148, cylindrical and of conductive material, extending inside drill bit 146 parallel to longitudinal axis L. In particular, first electrode 148 is arranged in a central bore of drill bit 146 and extends coaxially to longitudinal axis L up to a free end having first contact surface 149, which is flush with the external surface of drill bit 146 at tip 147.

Drill bit 146 also comprises second electrode 150, annular and of conductive material, extending along longitudinal axis L around first electrode 148. In particular, second electrode 150 is formed by a portion of drill bit 146 itself, made in this case of a conductive material. Second electrode 150 has second contact surface 151 composed of a cylindrical portion parallel to longitudinal axis L and corresponding to a lateral surface of drill bit 146, and an annular portion transverse to longitudinal axis L corresponding to a distal surface of drill bit 146.

A layer of electrically insulating material is interposed between first electrode 148 and second electrode 150 in such a manner that first contact surface 149 and second contact surface 151 can come into contact, at a distance from one another, with the anatomical portion during penetration of drill bit 146 into the anatomical portion. It should be understood, however, that the invention is not limited to the embodiment illustrated by drill bit 146, and other shapes are possible, such as, for example, that first electrode 148 and second electrode 150 are not arranged coaxially but may be formed from a rod of conductive material inserted into body 146. Furthermore, first electrode 148 and second electrode 150 each may have a point-like or other contact surface 149, 151 flush with the lateral surface or distal surface of drill bit 146. Alternatively, drill bit 146 could support two or more first electrodes 148 and two or more second electrodes 150.

Medical device 112 includes casing 152 to which proximal end 146*a* of drill bit 146 is integrally secured. Casing 152 has a housing that may enclose electronic components that enable medical device 112 to emit an appropriate warning signal. Those components include electric generator 154 and electric processing device 156 mounted on circuit board 158. Electric generator 154 is connected to first electrode 148 and second electrode 150, and is suitable for applying one or more voltages across first contact surface 149 and second contact surface 151. Processing device 156 may be connected to electric generator 154 and to first electrode 148 and second electrode 150, and is suitable for determining a measurement parameter related to the electrical characteristic based on a measurement electric current (s) induced by the applied voltage(s), and for emitting the warning signal corresponding to the measurement parameter. The measurement parameter may in particular be a voltage, an intensity of the electric current, conductivity or resistivity, or may be the result of processing one or more measurement electric currents, such as by integration, averaging, or the like.

Casing 152 also may enclose a device supplying electric power to electric generator 154 and processing device 156. It also may include a communication interface communicating with control unit 111 by any suitable means, wired or wirelessly, and optionally to workstation 118, e.g., to re-center the image or correct the relative position of the instrument image as compared to the anatomy.

In alternative embodiments, electric generator 154 and processing device 156, as well as the other electronic components of the medical device, could be located remote from the body of the medical device. For example, such components could be carried by robotic arm 134 or integrated into control unit 111.

To rotate drill bit 146 about longitudinal axis L, medical device 112 includes a drive mechanism, such as a gear motor assembly. In the first embodiment of FIG. 2, the drive mechanism may be mounted in housing 160 integral to effector 132 of robotic arm 134 so that, once integrally secured to the drive device, drill bit 146 is mounted on effector 132 of robotic arm 134.

Figure 4:
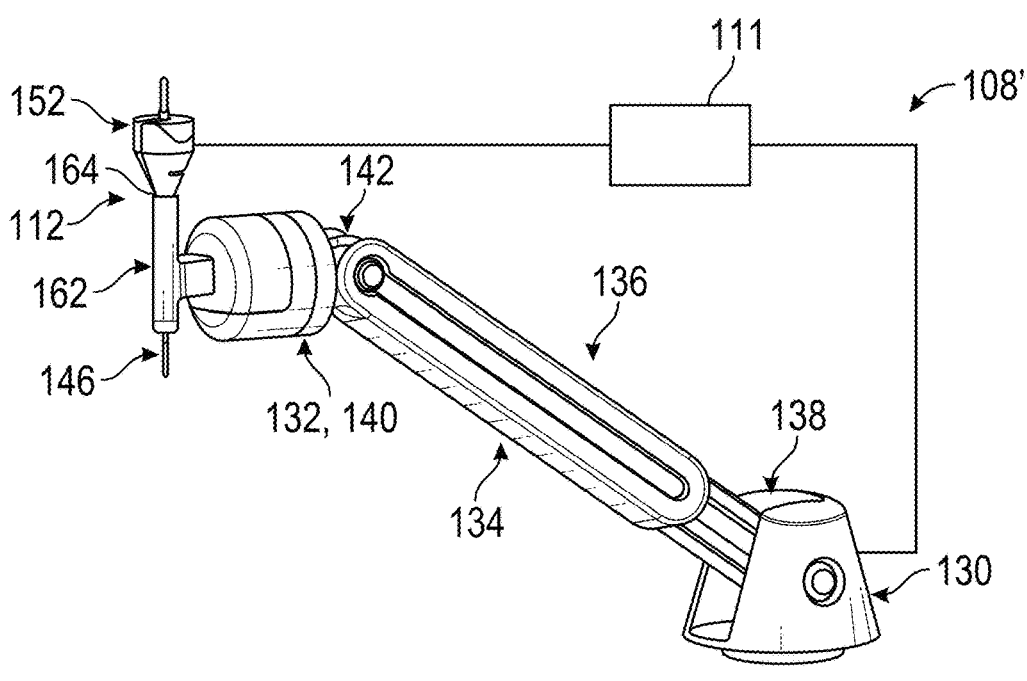
FIG. 4 is a schematic illustration of an alternative embodiment of the inventive system, in which the body of the medical device is configured to be moved by external action exerted on the medical device and in which the control unit is configured to issue a control signal as a function of the warning signal.

Referring now to FIG. 4, an alternative embodiment of portions of robot 108' constructed in accordance with the principles of the present invention is described. This alternative embodiment differs from the embodiment of FIG. 2 in that it is especially adapted to be implemented in a context of co-manipulation. As indicated above, medical device 112 of FIG. 2 may be operated independently of robotic arm 134, and movement of the drill bit may be obtained by an external action exerted on medical device 112 by the surgeon, for example. The actuators, or at least a portion of them, are reversible, in other words, they follow movement of the drill bit imposed by the external action, outside of particular situations identified further below.

Effector 132 of robotic arm 134 of FIG. 4 includes a stop member, making it possible to control movement of drill bit 146 at the appropriate time, as will be apparent from the following description. In particular, effector 132 of robotic arm 134 has duct 162 suitable for receiving drill bit 146. Duct 162 serves as a guide for drill bit 146 and also as a stop member. A portion of duct 162, and in particular upper edge 164, which defines an upper opening through which drill bit 146 is inserted into duct 162, may form the stop member that contacts the drilling device to control its movement when necessary. In this alternative embodiment, the drive mechanism for drill bit 146 is independent of effector 132 and, for example, may include a hand drill, not shown, held by the surgeon.

It should be noted that co-manipulation also may be obtained with medical system 100 according to the embodiment of FIG. 2, such that the surgeon exerts an external action on drilling device 112 either directly, by manipulating the drilling device, or indirectly, by manipulating effector 132. Drilling device 112 also may be manipulated in co-manipulation scheme by means of a robotic arm that includes a stop member other than robotic arm 134. In addition, the stop member may be implemented in any other suitable manner so as to come into contact with drilling device 112 to control movement of drill bit 146. The other features of operating environment in which robot 108' according to the embodiment of FIG. 4 is used are similar to those of operating environment 100 according to the embodiment of FIG. 2, and such further details are provided herein above.

Figure 5:
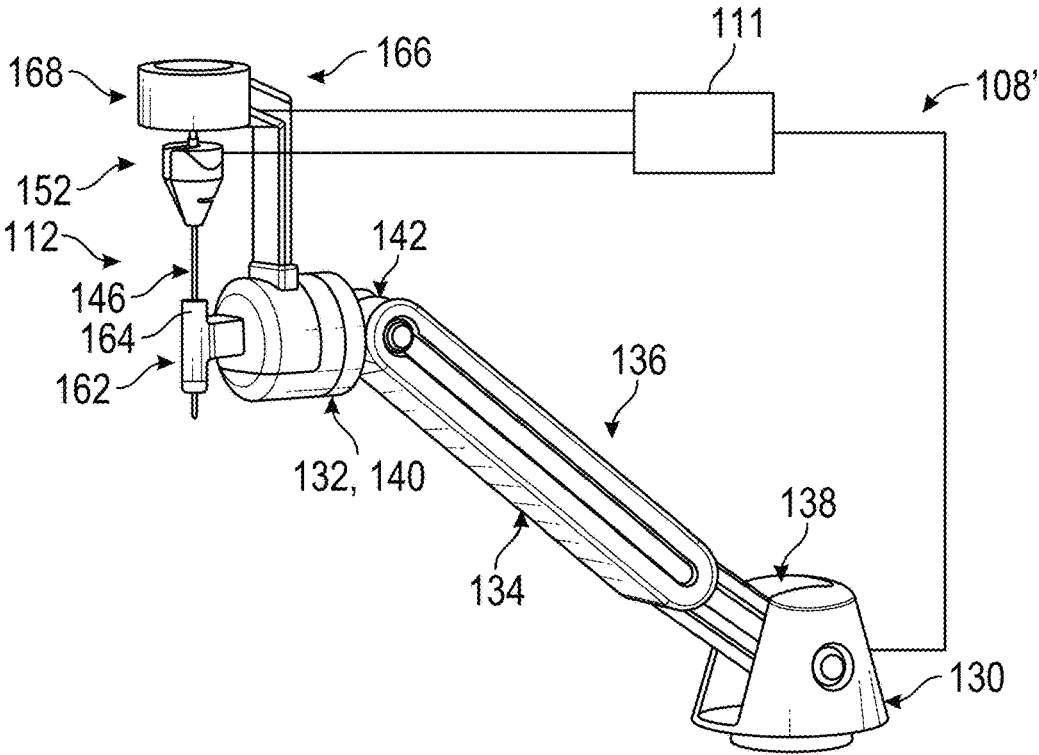
FIG. 5 is a schematic illustration of a further embodiment of the invention, in which the effector includes a duct and a support that is movable relative to the duct, such that the body of the medical device is mounted on the support and the control signal instructions direct movement of the support relative to the duct.

FIG. 5 depicts robot 108" according to a further alternative embodiment of the invention. In the embodiment of FIG. 5, effector 132 of robotic arm 134 includes duct 152 similar to the one previously described with respect to the embodiment of FIG. 4. Effector 132 includes support 166 that is movable relative to duct 162, and on which drill bit 146 is mounted. In particular, in the embodiment of FIG. 5, support 166 is movable in translation along a central axis of duct 162. Alternatively, any other movement of support 166 relative to duct 162 could be provided. Support 166 carries housing 168, which contains the drive mechanism to which the drill bit can be secured for rotation through duct 162. As indicated above, duct 162 also may serve as a guide and stop member.

In accordance with one aspect of the invention, control unit 111 preferably is configured to issue a control signal that controls the movement of effector 132 relative to base 130 as a function of the warning signal emitted by drilling device 112 when drill bit 146 is penetrating targeted tissue.

Figure 6:
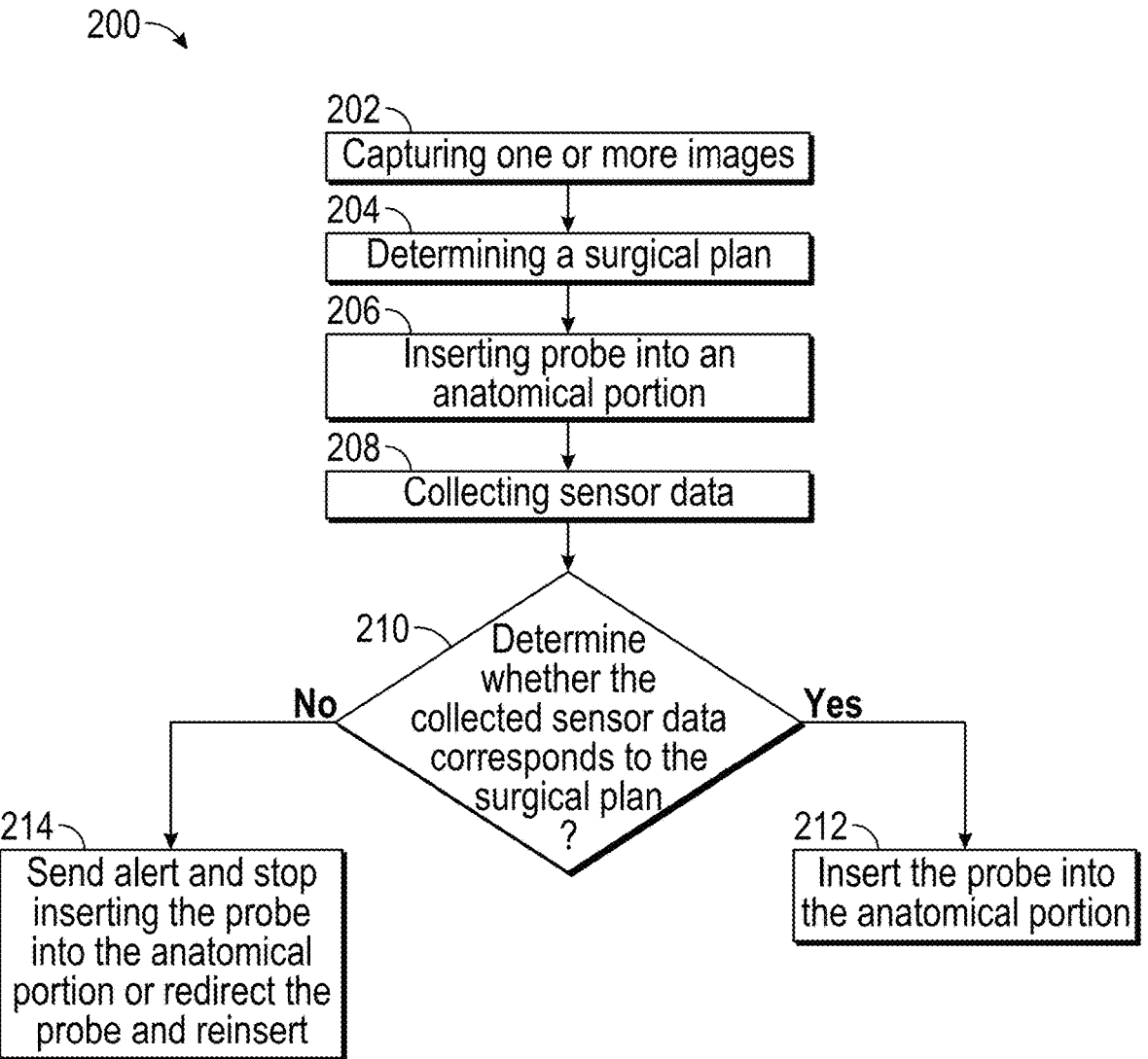
FIG. 6 is a flowchart illustrating a method of a surgical navigation procedure of the present invention.
Figure 7A:
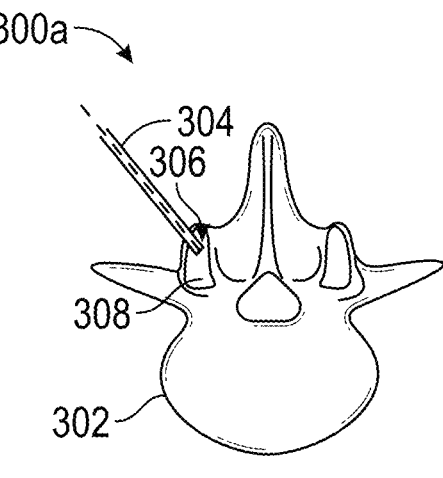
FIGS. 7A to 7C are illustrative examples of implementation of the surgical navigation procedure of the present invention.
Figure 7B:
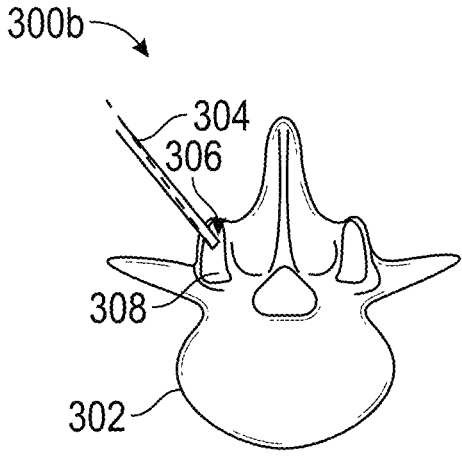
Figure 7C:
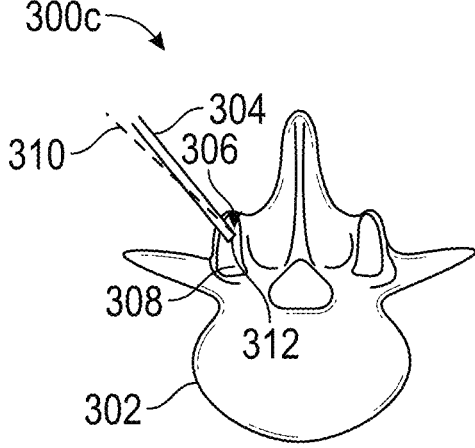

Referring now to FIGS. 6 and 7A-7C, a flowchart illustrating method 200 for conducting a surgical procedure according to one aspect of the present invention, for example as depicted in FIGS. 7A-7C, is described. FIGS. 7A, 7B and 7C illustrate exemplary surgical procedures 300a, 300b and 300c to be carried out in accordance with method 200.

Referring still to FIG. 6, a plurality of images of a target anatomy are captured at step 202, for example, using imaging system 104 of FIG. 1. The captured images may be CT images and/or x-ray images of the anatomical portion of patient P where a surgical procedure will be performed. The CT images, and/or x-ray images may be collected when patient P is positioned lying on surgical table 128 within arm 126 of imaging system 104, or more preferably, are taken at a time prior to performing the surgical procedure. The images may be taken from two orthogonal directions, such as anterior-posterior (A-P) and lateral, of the anatomical portion, e.g., a portion of 302 vertebra, such as a pedicle, of patient P. Imaging system 104 may transmit the acquired images from image receiving section 122 to workstation 118 and/or precision guidance system 102.

A surgical plan is determined at step 204 and a user, e.g., a surgeon, may input the surgical plan to be executed by precision guidance system 102. Based on the captured images, the surgeon may determine the surgical plan to implant and/or determine a trajectory placement of a surgical device or implant, such as a pedicle screw. The surgical plan may include the path, such as path 304, to implant the surgical device into the anatomical portion of patient P. For example, the surgeon may determine that a hole configured to receive a pedicle screw may be formed via path 304, as shown in FIGS. 7A-7C. The surgeon may determine that path 304 enters into central portion 306 of left pedicle 308 of vertebra 302. The surgeon, using the captured images, may determine data related to the anatomical portion, e.g., the bone type of the anatomical portion and/or the bone type around path 304.

Having determined the surgical plan, the plan then may be imported into workstation 118 and/or precision guidance system 102. A mounting platform, such as a fixation bone clamp of precision guidance system 102 as described in U.S. Pat. No. 9,066,751, which is incorporated herein by reference in its entirety, may be rigidly attached to the patient at another anatomical portion, such as a spinous process of another vertebra either above or below the target vertebra, of the patient. Alternatively, a mounting platform, such as a percutaneous reference pin for use with precision guidance system 102, may be rigidly attached to the patient at another anatomical portion, such as the posterior superior iliac spine. Precision guidance system 102 may perform a 3D scan of the surgical location, via camera 110 and/or a 3D camera integrated into robotic 108, to reconstruct the 3D volume of patient P and assess the working area for the surgeon. The one or more captured images may be mapped to the 3D scan of the surgical location.

A medical tool, such as a probe or drilling device, is inserted at step 206 into the anatomical location. Robot 108 may begin to insert the probe, e.g. drilling device 112, into the anatomical portion, e.g., left pedicle 306 of vertebra 302 of patient P. As the probe is inserted into the anatomical portion, sensor data is collected at step 208, preferably by electrodes 148 and 150 of device 112. The probe may transmit the collected sensor data to precision guidance system 102, via a suitable wired or wireless arrangement. Precision guidance system 102 may be configured to convert the collected sensor data to impedance values or measures of bone density and/or tissue density. Medical device 112 may transmit the collected sensor data to precision guidance system 102, which analyzes the collected sensor data in real-time.

Having analyzed the collected sensor data, a determination is made at step 210, preferably by precision guidance system 102, whether the collected sensor data corresponds to the surgical plan. For example, precision guidance system 102 may determine whether the collected sensor data corresponds to the surgical plan in periodic time increments. Precision guidance system 102 also may continuously evaluate whether the collected sensor data corresponds to the surgical plan while the drilling device penetrates into the anatomical location. When the surgical plan is created using the captured images, precision guidance system 102 may determine data related to the anatomical portion. For example, precision guidance system 102 may determine at least one of the bone density and the tissue density of the anatomical portion and/or at least one of the bone density and the tissue density around path 304. To determine whether the collected sensor data corresponds to the surgical plan, precision guidance system 102 may compare the collected sensor data to the data of the anatomical portion predicted in the surgical plan. For example, for the cases in which the collected sensor data relates to bone impedance values, the collected sensor data may be compared to the predetermined bone impedance value of the anatomical portion.

For the cases in which the collected sensor data corresponds to the surgical plan (at decision step 210: YES), the drilling device continues penetrating into anatomical portion at 212. For example, precision guidance system 102 determines that path 304 measured by the sensors corresponds to path 204 determined by the surgical plan. That is, the impedance values collected by electrodes 148, 150 corresponds to the electrical characteristics predetermined in the surgical plan. In example 300*a*, precision guidance system 102 determines that the collected sensor data places path 304 on an equivalent path or almost equivalent path as path 304 determined by the surgical plan. In this case, precision guidance system 102 determines that the impedance values measured by the sensors while traveling along path 304 correspond to the predetermined electrical characteristics of vertebral body 302. In example 300*b*, precision guidance system 102 determines that the collected sensor data places path 304 slightly angled and/or off center from path 204; however, precision guidance system 102 determines that the collected sensor data is within an acceptable range of path 304. That is, the impedance values of the anatomical portion measured by the sensors may not be equivalent to the predetermined electrical characteristics; however, the values measured by the sensors may be close enough to the predetermined values to be acceptable for precision guidance system 102, e.g., within 5-10%. In this case, robot 108 continues to insert the drilling device into left pedicle 308 of the vertebra 302.

For the cases in which the collected sensor data does not correspond to the surgical plan (at decision step 210: NO), an alert is sent and the insertion of the probe into the anatomical location may be stopped at 214. For example, the collected sensor data may not correspond to the surgical plan when the impedance values collected by the sensors is not equivalent to the predetermined electrical characteristics in the surgical plan, and/or the data collected by the sensors falls outside of the acceptable range of the predetermined values. For these cases, precision guidance system 102 may send an alert to the surgeon that the collected sensor data does not correspond to the surgical plan, and/or stop robot 108 from further inserting the drilling device into the anatomical location.

The alert may be provided as an alarm, message, feedback, or in other suitable manner. For example, the alert may constitute a graduated visual signal and/or audio signal. For cases in which the impedance data collected by the sensors deviates from the surgical plan, a visual signal may appear on monitor 106 and/or workstation monitor 120. For instance, if precision guidance system 102 determines that the data collected by the sensors deviates at or about 1% from the predetermined data in the surgical plan, a yellow warning light may appear on monitor 106. In another instance, if precision guidance system 102 determines that the data collected by the sensors deviates at or about 10% from the predetermined data in the surgical plan, an orange warning light may appear on monitor 106. Still further, if precision guidance system 102 determines that the data collected by the sensors deviates at or about 20% from the predetermined data in the surgical plan, a red warning light may appear on monitor 106.

In an alternative embodiment, instead of visual warning signals, the alerts and warnings may manifest as audible tones, which enables the surgeon to monitor the progress of the surgical plan without diverting his attention to monitors 106 or 120. In such an embodiment, a simple tone may be emitted from the precision guidance system if the deviation between measured and plan impedance values differs by 1% or less. If the measured values deviate from plan by about 10%, a second audio signal may be emitted as a more complex tone than the tone of the first audio signal. Further, if the deviation from surgical plan exceeds about 20%, a third audio signal may be emitted as a more complex tone than the tone of the second audio signal.

Precision guidance system 102 may automatically stop robot 108 in those cases for which the collected sensor data does not correspond to the surgical plan. In addition, the surgeon may manually stop, redirect or interrupt the automatic or manual insertion upon receiving or perceiving the alert.

In the scenario depicted in FIG. 7C, precision guidance system 102 determines that the collected sensor data places path 310 outside an acceptable range of path 304. For instance, path 310 may be at a different insertion angle than path 304, and/or path 310 may extend beyond the predetermined end of path 304. That is, precision guidance system 102 may determine that impedance values measured by the sensors while traveling along path 310 do not correspond to the predetermined electrical characteristics of vertebral body 302. Determining that path 310 is outside the acceptable range for path 304, precision guidance system 102 stops advancement of drilling device 112 probe into left pedicle 308 and issues an alert to the surgeon to indicate that robot 108 is not following path 304 of the surgical plan. Precision guidance system 102 may issue instructions to stop inserting drilling device 112 when the insertion angle of path 310 is determined to be incorrect or path 310 extends beyond an end portion 312 of path 304 determined by the surgical plan.

Precision guidance system 102 also may be configured to assess the collected sensor data to determine whether drilling device 112 is askew. For example, precision guidance system 102 may determine whether the impedance values from the sensors are within an acceptable range. If, for instance, precision guidance system 102 senses a deviation that is not within an acceptable range, precision guidance system 102 may determine that the probe is skewed and compute a revised trajectory to reduce the deviation to an acceptable level, for example, using a multiple electrode arrangement as described in commonly-assigned U.S. Pat. No. 8,419,746, the entirety of which is incorporated herein by reference. Such a revised trajectory may be communicated to the surgeon by directional arrows on monitor 106 showing a revised insertion angle. In this manner, data from the sensors may be used to provide an additional source of data to the surgeon to confirm or improve the accuracy of execution of the surgical plan. The sensor data may serve as a feedback mechanism for precision guidance system 102 to provide a high degree of confidence in the accuracy of path 304.

Alternatively, control unit 111 may be programmed to generate a series of micro-motions of tip 147 during advancement of drill bit 146, for example, by vertical, angular and/or lateral displacements of tip 147 of up to 1 mm in directions spaced at 90 degrees around the bore hole created by drill tip 147 to determine impedance values in each of the corresponding quadrants. Such motions may include, for example, reversing drill bit 146, removing the shaft of the drill bit from a current bore, slightly changing the angulation or location of the entry point of 147, and again advancing the drill bit. By storing and comparing the sensed impedances resulting from the micro-motions, control unit may determine when tip 147 is nearing a transition in tissue electrical characteristics, and thus steer further advancement of drill bit 146 in the direction that most closely aligns with the predetermined path of the surgical plan. Control unit 111 again may be programmed to provide such feedback to the surgeon, or to assist in visualizing such trajectory corrections, by superimposing a revised computed trajectory on monitor 106 of precision guidance system 102. As a further alternative, if the trajectory corrections computed based on the micro-motion displacements are not directly provided to robot 108 to effectuate the trajectory, the suggested trajectory corrections may be visually communicated to the surgeon by directional arrows superimposed on the images of the anatomical portion displayed on monitor 106.

Referring now to FIGS. 8 to 15, vertebra 320 is a boney structure internally comprising foramen 321 traversed by the spinal cord and vascular structures. On a dorsal face, vertebra 320 has spinous process 322 extending in a sagittal plane and two transverse processes 323 extending substantially one on each side of foramen 321 in a frontal plane, with nerve endings passing nearby. Vertebra 320 is externally delimited by outer layer 324 of cortical bone. Foramen 321 is itself delimited by inner layer 325 of cortical bone. Between outer layer 324 and inner layer 325 of cortical bone is cancellous bone 326. Inner layer 325 and outer layer 324 of cortical bone each constitute a first medium having a first capacity to conduct electric current. The cancellous bone constitutes a second medium having a second capacity to conduct electric current, the second capacity being greater than the first capacity. Soft tissues and fluids, such as blood, surrounding outer layer 324 of cortical bone and inside inner layer 325 of cortical bone constitute a third medium having a third capacity to conduct current, the third capacity being greater than the first and second capacities.

Figure 8:
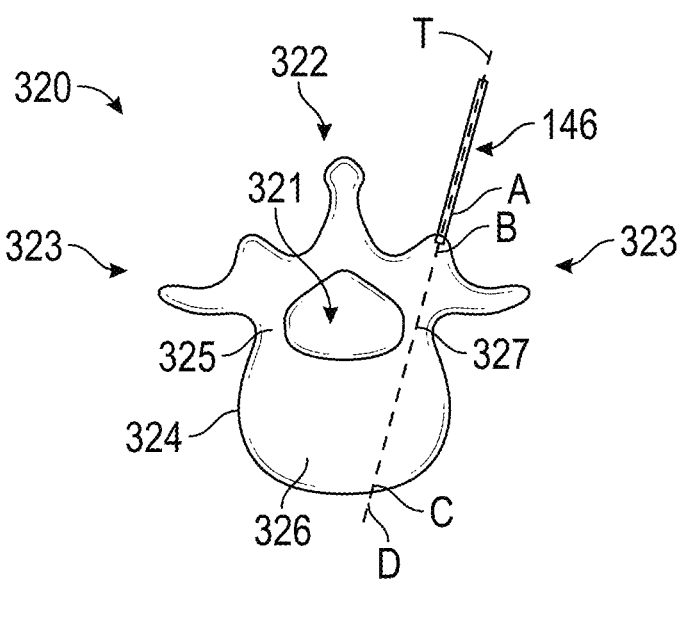
FIG. 8 is an exemplary illustration showing penetration of a spinal pedicle and vertebrae, and the corresponding transitions in the sensed electrical characteristics, and changes in control unit instructions provided to the medical device.
Figure 8:
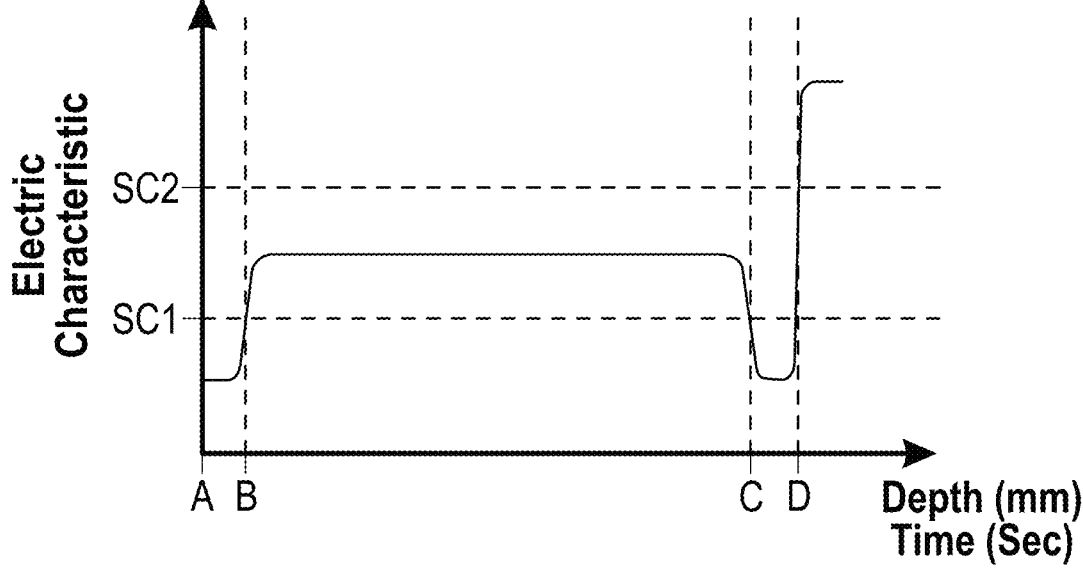
Figure 8:
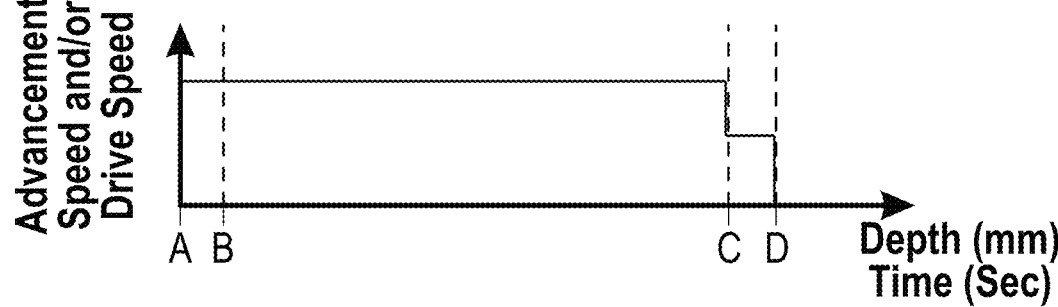

FIG. 8 illustrates an exemplary control signal issued by precision guidance system 102 during penetration of drill bit 146 into pedicle 327 of vertebra 320 from entry point A in outer layer 324 of cortical bone to first exit point C in outer layer 324 of cortical bone opposite the entry point A. Longitudinal axis L of drill bit 146 is placed along a predetermined penetration direction T and tip 147 of drill bit 146 is brought into contact with outer layer 324 of cortical bone at the entry point A. Examples of determining the entry point and penetration direction T of the body of a medical device intended to penetrate an anatomical portion are described, for example, in above-incorporated U.S. Pat. No. 8,419,746.

Still referring to FIG. 8, the measurement parameter representative of the electrical characteristic taken into account is an intensity of a measurement electric current flowing between first contact surface 149 and second contact surface 151, representative of a conductivity of the medium in which tip 147 of drill bit 146 is located. The warning signal emitted therefore corresponds to this intensity.

At entry point A, tip 147 of drill bit 146 is in contact with cortical bone. When approaching interface B at the transition between cortical bone 324 and cancellous bone 326 from the outer layer of the cortical bone, tip 147 of the drill bit 146 approaches the cancellous bone. Because the conductivity of cortical bone is lower than that of cancellous bone, the current intensity between first contact surface 149 and second contact surface 151 increases. While traversing the cancellous bone by passing through one of pedicles 327 and until encountering outer layer 324 of cortical bone at exit point C, the intensity remains substantially unchanged and the warning signal reaches a plateau. At exit point C, when tip 147 again approaches cortical bone 324 and begins penetrating into the outer layer of cortical bone, the measured current intensity decreases. While drilling through outer layer of cortical bone 324, tip 147 of drill bit 146 approaches interface D between the cortical bone and the medium composed of soft tissue and fluids, such as blood, which have a higher conductivity than that of cortical bone and cancellous bone. Thus, measured current intensity between electrodes 148 and 150 increases, until a new plateau is reached, when tip 147 crosses the outer layer of cortical bone 324.

Figure 9:
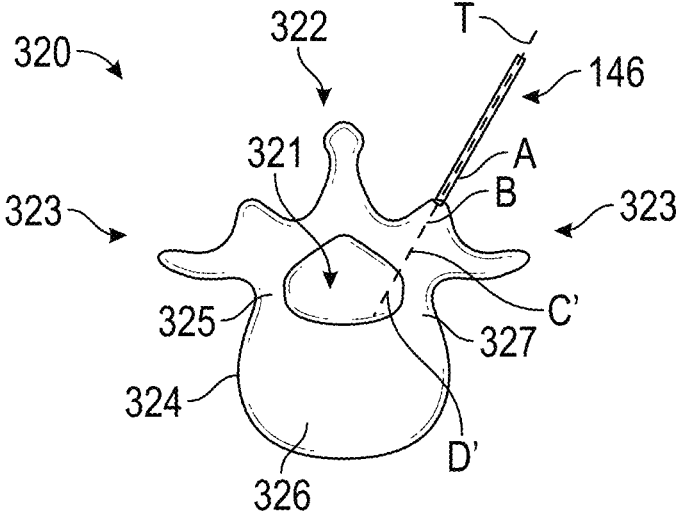
FIGS. 9 through 15 are an exemplary illustrations, similar to that of FIG. 8, for different initial trajectories of the medical device.
Figure 9:
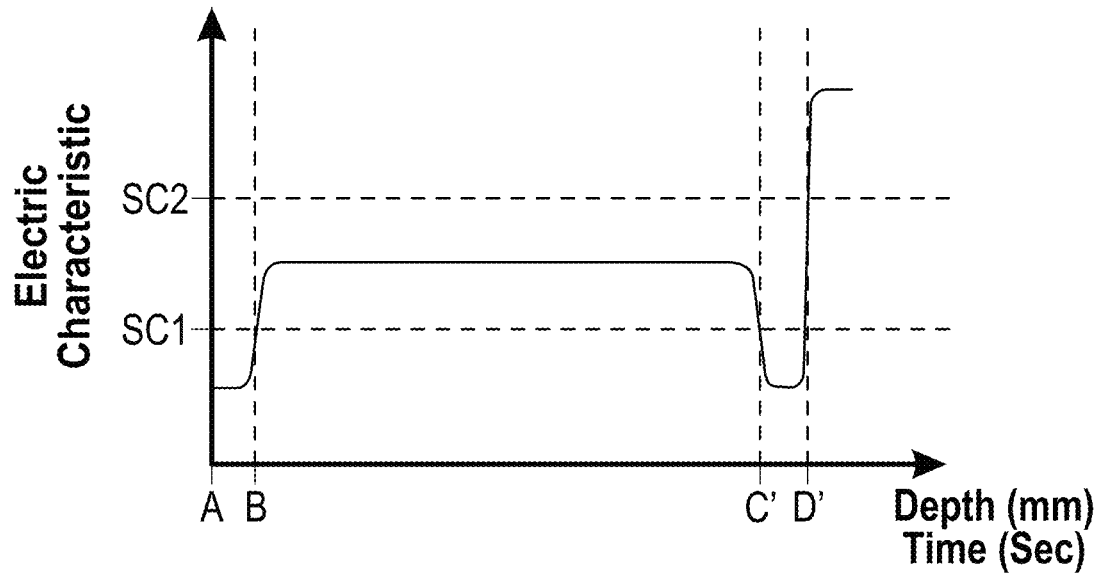
Figure 9:
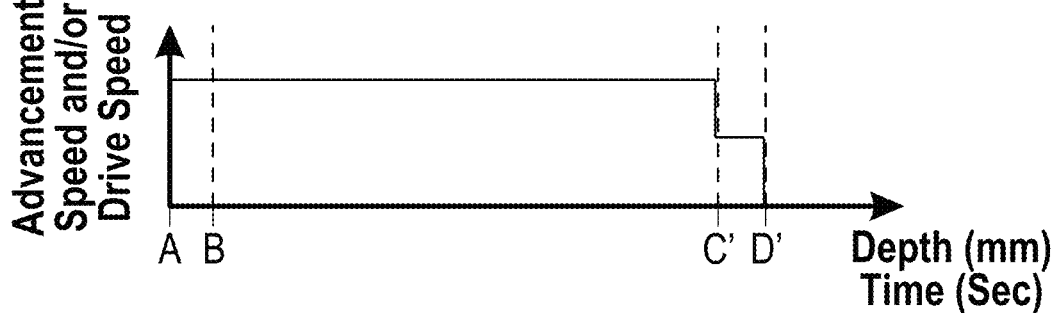

FIG. 9 depicts generation of a similar warning signal during penetration of drill bit 146 into pedicle 327 of vertebra 320 from entry point A into outer layer 324 of cortical bone up to a second exit point C' into inner layer 325 of cortical bone defining foramen 321. In effect, drill bit 146 again successively crosses cortical bone in outer layer 324 of cortical bone, then cancellous bone, and then cortical bone in inner layer 325 of cortical bone, before reaching a medium composed of soft tissue and fluids, such as blood, in foramen 321. The warning signal thus may be used to determine a position of tip 147 of drill bit 146 relative to the boney structure of vertebra 320.

By choosing one or more critical thresholds, each representative of a critical position of tip 147 of drill bit 146 relative to the boney structure of vertebra 320, and by comparing an absolute value at each instant or a variation over a defined period of the measurement parameter at the corresponding critical threshold, it is possible to control the movement of drill bit 146 by means of the control signal provided by precision guidance system 102. A critical position is understood to mean a position for which its differentiation from other positions is of interest. It may be a position presenting a risk to the patient, but not necessarily. In order to be able to make the comparison, the critical threshold is an absolute value or a variation of a reference parameter comparable to the measurement parameter. The reference parameter may be predetermined based on test results on reference anatomical structures, it may be chosen by a user, or may be defined in any suitable manner.

For example, control unit 111 may detect interface B between cancellous bone and cortical bone when the warning signal corresponding to the current intensity between first contact surface 148 and second contact surface 151 varies by decreasing to below first critical threshold SC1. Control unit 111 also may detect a breach in one of inner 325 and outer 324 layers of cortical bone when the warning signal once again increases beyond a minimum value of the measurement parameter representative of cancellous bone with a defined deviation. The deviation from the minimum value of the measurement parameter representative of cancellous bone may constitutes second critical threshold SC2, as depicted in FIG. 8.

The minimum value of the measurement parameter representative of cancellous bone may be defined in a differential manner during drilling of vertebra 320. For example, control unit 111 of precision guidance system 102 may assign an initial value to the minimum value of the measurement parameter and continuously measure a current value of the measurement parameter. As long as the warning signal does not exceed first critical threshold SC, if the current value of the measurement parameter is less than the minimum value of the measurement parameter, control unit 111 assigns the current value of the measurement parameter to the minimum value of the measurement parameter.

More generally, when the anatomical portion includes a first medium having a first capacity to conduct electric current, a second medium having a second capacity to conduct electric current, the second capacity being greater than the first capacity, and a third medium delimited by the first medium and having a fluid with a third capacity to conduct current, the third capacity being greater than the first and second capacities, control unit 111 of precision guidance system 102 may be configured to: detect an interface between the second medium and the first medium, such that the warning signal varies in a first variation direction and passes beyond a first critical threshold; detect a breach in the first medium when, after having varied in the first variation direction with respect to the threshold, the warning signal varies in a second variation direction opposite to the first variation direction, such that the warning signal passes beyond a minimum value of the measurement parameter representative of the second medium with a defined deviation.

The minimum value of the measurement parameter representative of the second medium may be obtained as described above in relation to the boney structure. The movement of drill bit 146 may be defined by several movement parameters including: penetration direction T, an advancement direction (drawing closer to the bone structure), a reverse direction (moving away from the bone structure) which are opposite one another along penetration direction T, a trajectory adjustment (away from a detected transition), a variable advancement or reverse speed and a variable advancement or reverse force.

As long as the warning signal has not reached a critical threshold, the control unit issues a control signal authorizing movement of the drill bit in the advancement direction along penetration direction T relative to the boney structure of the vertebra.

Referring now to FIGS. 8 and 9, the control signal may include instructions for reducing the advancement speed of drill bit 146 in the advancement direction when the warning signal reaches first critical threshold SC1. In addition, the control signal may include instructions for reducing the drive speed of drill bit 146 in the first direction of rotation when the warning signal reaches first critical threshold SC1. In the case of controlling the force, it would be the advancement force that would be reduced.

When the warning signal reaches second critical threshold SC2 (deviation from the minimum value of the measurement parameter representative of cancellous bone), the control signal may include instructions for stopping the movement of drill bit 146 relative to the boney structure of the vertebra and interrupting the rotation of drill bit 146.

Alternatively, any other control of the movement of drill bit 146, and more generally of the body of the medical device, could be provided by issuing the appropriate control signal with the corresponding movement parameters. In particular, when the warning signal reaches a critical threshold corresponding to breaching cortical bone, such as second critical threshold SC2 described above, control unit 111 may issue a control signal including instructions for stopping, moving in the advancement direction and reverse direction over specified ranges to follow the patient's respiratory movements. The control signal also may be adapted to the risks represented by damage to a given medium. For example, in the absence of an immediate major risk, detection of damage to a layer of cortical bone by crossing a corresponding critical threshold, such as first critical threshold SC1 described above, could cause control unit 111 to reduce the advancement speed but increase the drive speed in the first direction of rotation to take into account the greater hardness of cortical bone compared to that of cancellous bone.

To ensure continuous and real-time control of the movement of drill bit 146, the measurement electric current has a measurement period that is less than the ratio of a critical distance of drill bit 146 in the advancement direction along penetration direction T, to the advancement speed of drill bit 146, the critical distance being in particular less than or equal to 1 mm. Electric generator 154 of drilling device 112 may be connected to control unit 111 and the control unit may be suitable for measuring the advancement speed of drill bit 146 and for controlling electric generator 154 so that it applies the appropriate measurement electric current.

To improve control over the movement of drill bit 146, in addition to the warning signal, control unit 111 may issue the control signal as a function of one or more other signals. The combination of the warning signal providing information on the electrical characteristic of the medium along with other signals can enable differentiating between different mediums having similar capacities to conduct electric current. The actual position of drill bit 146 relative to the boney structure of the vertebra thus may be defined more precisely, and the control signal adapted accordingly.

In accordance with another aspect of the invention, the medical system may comprise a depth detection device connected to control unit 111 and configured to emit a depth signal corresponding to the depth to which drill bit 146 has penetrated the boney structure of the vertebra. The depth detection device may be of any suitable type, and may include, for example, one or more position sensors integrated into robot 108 that make it possible to determine the depth based on displacements of the robot actuators. As an alternative, the depth detection device may comprise one or more external sensors, for example optical sensors, that detect markings on the exterior of drill bit 146.

Accordingly, in FIGS. 8 and 9, based on the combination of warning and depth signals, control unit 111 may determine which among inner layer 325 and outer layer 324 of cortical bone has been reached after having passed through the cancellous bone and, where appropriate, issue different control signals depending on the layer of cortical bone reached. For example, a reduction in the advancement speed could be greater when inner layer 325 of cortical bone is reached than when outer layer 324 of cortical bone is reached. Or, it could be provided to impose a reverse speed and drive drill bit 146 in a second direction of rotation upon reaching inner layer 325 of cortical bone, while it would be provided to reduce the advancement speed and the drive speed in the first direction of rotation upon reaching outer layer 324 of cortical bone.

Figure 10:
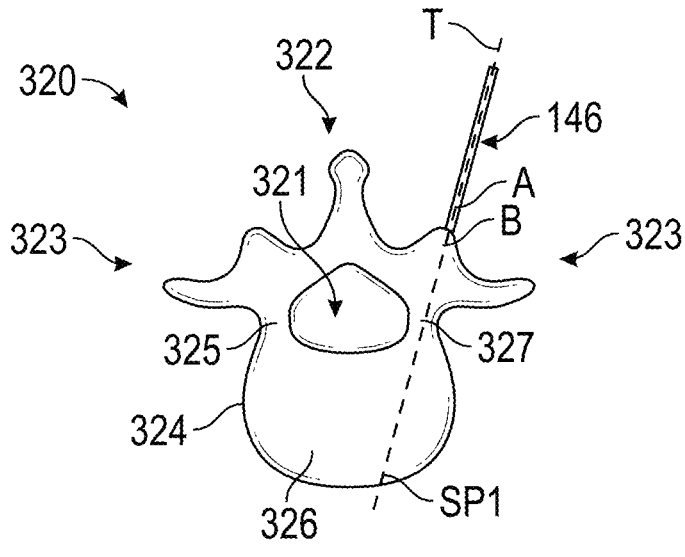
Figure 10:
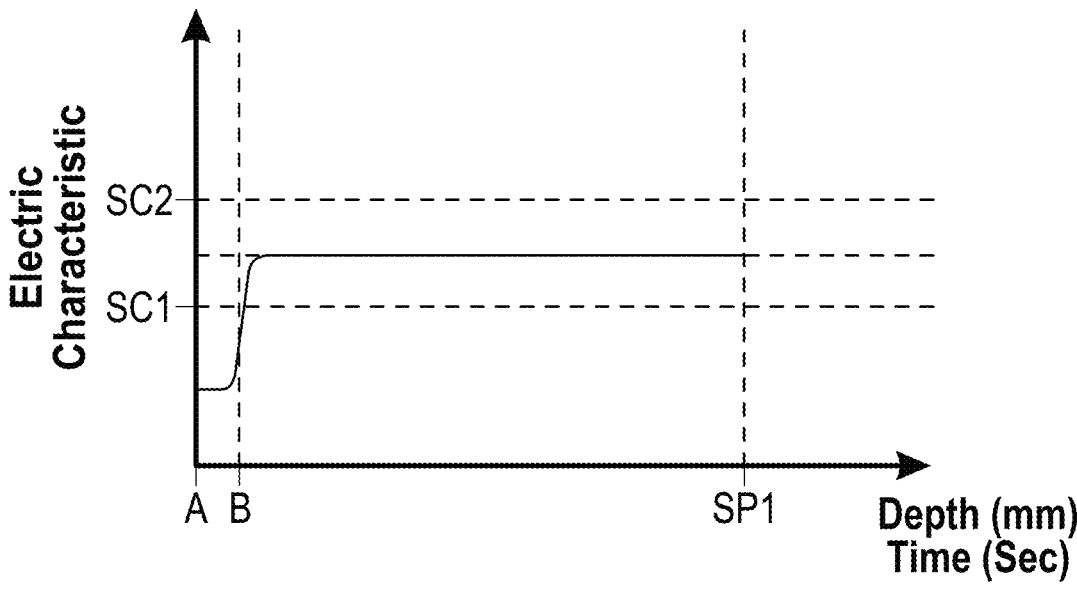
Figure 10:
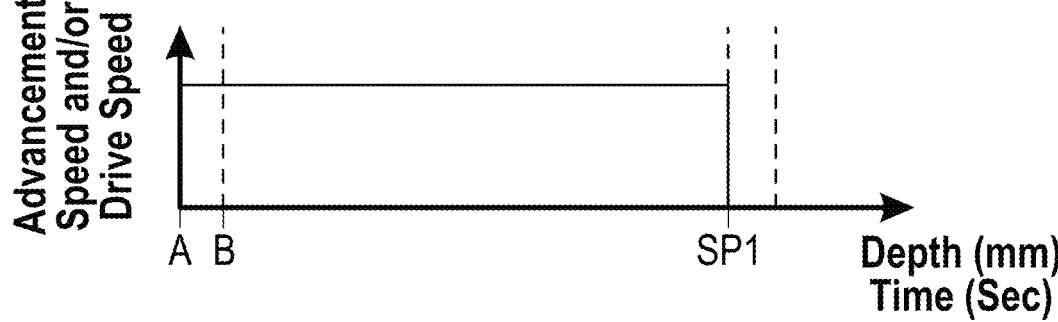

FIG. 10 depicts an example of a control signal starting from when a depth threshold SP1 is reached. The control signal modifies the movement of drill bit 146 when one among critical thresholds SC1 and SC2 and depth threshold SP is reached. The control signal may include instructions enabling movement of drill bit 146 in the advancement direction along the penetration direction T at an advancement speed, from entry point A of outer layer 324 of cortical bone, as long as the depth signal has not reached depth threshold SP1. In the absence of detecting that one of critical thresholds SC1, SC2 has been exceeded, movement of drill bit 146 continues until the depth signal reaches depth threshold SP1 indicating that tip 147 of drill bit 146 is positioned at a target depth, for example corresponding to a length of a pedicle screw to be implanted. In FIG. 10, when the depth threshold SP1 is reached, the control signal reduces the speed of drill bit 146 to stop it, it being understood that any other change to the movement or direction of drill bit 146 could be undertaken. For example, the control signal could include instructions for moving the drill bit in a reverse direction along penetration direction T, reduce either or both of the advancement speed and force of the drill bit, or redirect the drill bit.

In accordance with yet another aspect of the invention, control unit 111 may include several predefined signatures. Each signature may include a reference warning signal resulting from a variation of the measurement parameter related to the electrical characteristic during penetration of drill bit 146 into a reference anatomical portion. Each signature also may combine the reference warning signal with a reference depth signal resulting from a variation of a depth parameter related to the depth to which drill bit 146 has entered the reference anatomical portion. Each signature further may include a corresponding set of movement parameters, at least some of them possibly different from the movement parameters of the other sets of movement parameters. These movement parameters also may include the critical threshold(s), the depth threshold(s), or other parameters.

The warning signal thus may be analyzed differently, in particular with respect to the exceeding of certain critical thresholds, depending on the actual position of drill bit 146 relative to the boney structure of the vertebra. More spe-cifically, control unit 111 may be configured so that, during penetration of drill bit 146 into a vertebra, it continuously saves the measurement parameter and compares the variation of the measurement parameter with the signatures. If the variation of the measurement parameter corresponds to one of the signatures, the control unit issues the control signal with the set of movement parameters corresponding to that signature.

For example, the variation in intensity as the measurement parameter with respect to the depth illustrated in FIG. 9 may constitute an internal breach signature representative of drilling vertebra 320 from an entry point facing pedicle 327 and along a path leading to breaching inner layer 325 of cortical bone. The variation in intensity as the measurement parameter with respect to the depth illustrated in FIG. 10 may constitute an expected signature representative of drilling vertebra 320, which may be qualified as suitable for placement of a pedicle screw from an entry point facing pedicle 327 and along a path leading to a defined depth through the pedicle.

Figure 11:
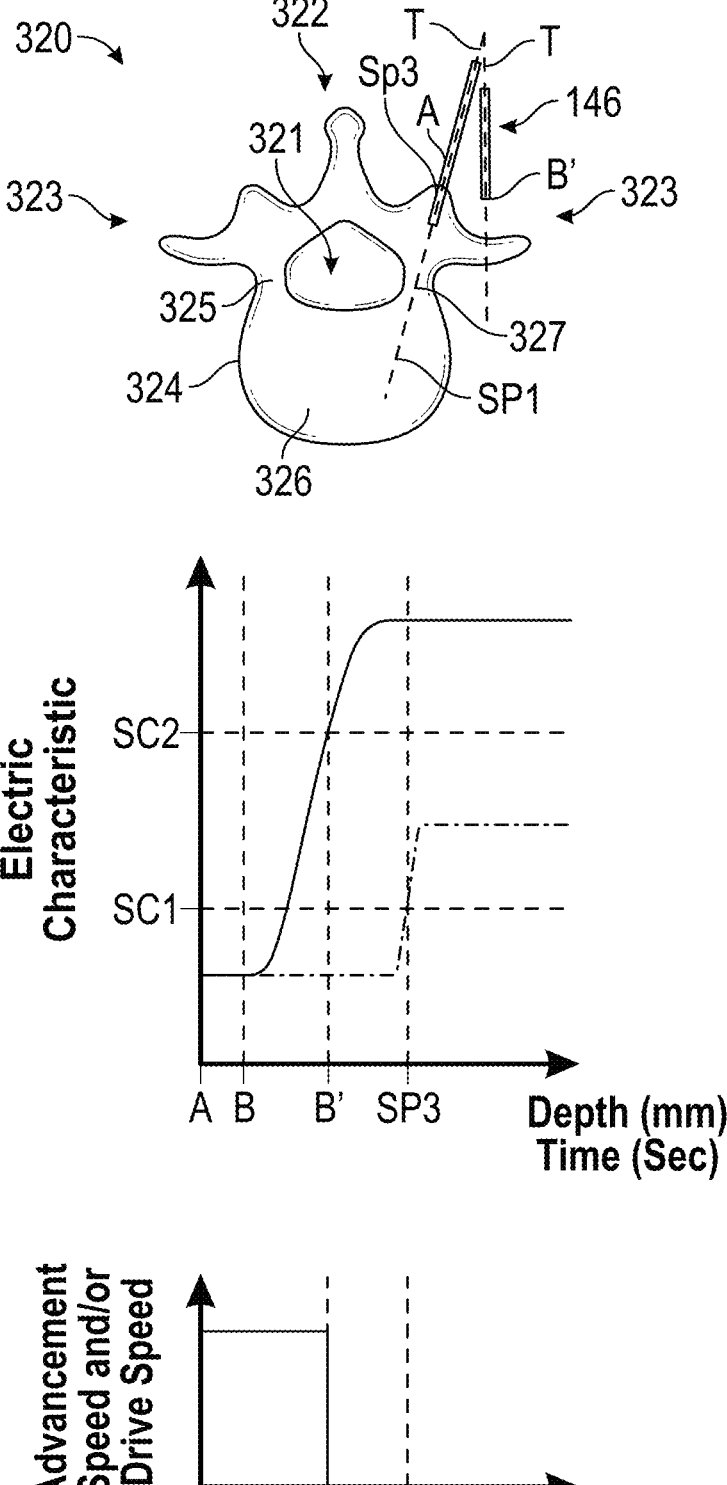

FIG. 11 illustrates the detection of a sliding of drill bit 146 on outer layer 324 of cortical bone. Tip 147 of drill bit 146 is positioned on the predetermined entry point A, but slides to another location B' on outer layer 325 of the cortical bone, at a distance from the predetermined entry point A. In accordance with the expected signature represented by the dotted line, the current intensity as a measurement parameter should be constant at a level corresponding to that of cortical bone and then should increase to the level of intensity of cancellous bone, such that the depth signal reaches third depth threshold SP3, for example about 5 mm, corresponding to the interface between cortical bone and cancellous bone. In the case of sliding of drill bit 146 as depicted in FIG. 11, instead of being located in cortical bone, tip 147 of the drill bit enters the soft tissue and fluids surrounding vertebra 320, where the conductivity is higher than that of cancellous bone. Before the depth signal reaches third depth threshold SP3, the warning signal exceeds second critical threshold SC2 representative of breaching the cortical bone and the control unit shuts down drill bit 146.

Figure 12:
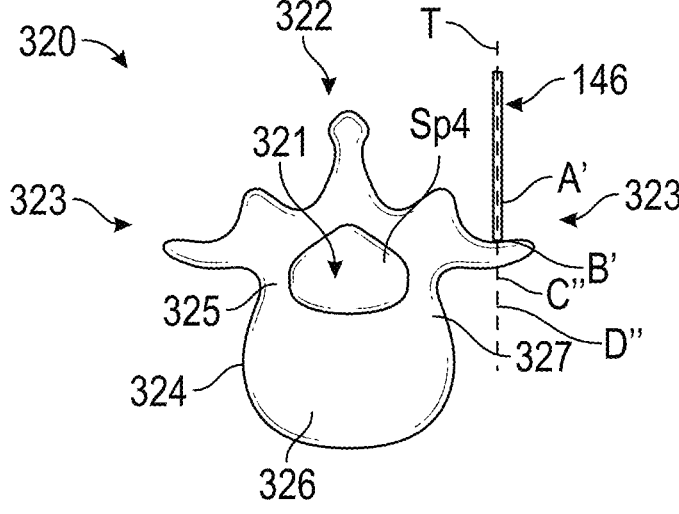
Figure 12:
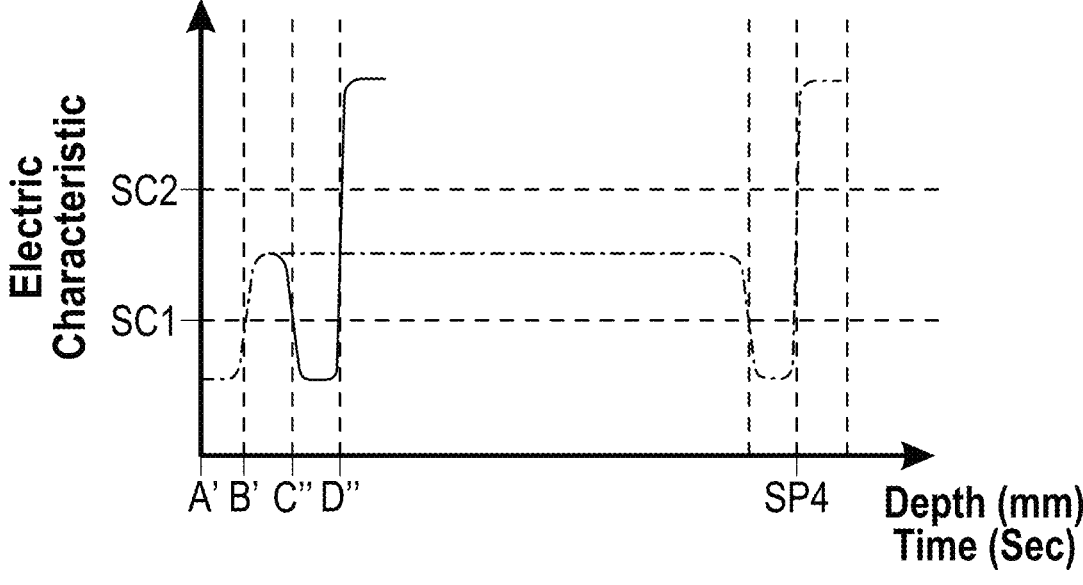
Figure 12:

FIG. 12 depicts detection of traversing one of transverse processes 323, based on internal breach and/or expected signatures as represented by a dotted line. According to the internal breach signature, no breach should be detected by the second critical threshold SC2 being exceeded by the warning signal before fourth depth threshold SP4 is reached. When traversing transverse process 323, tip 147 of drill bit 146 is positioned at a predetermined location A', but penetration direction T leads it to successively cross outer layer 324 of cortical bone, cancellous bone, and again the outer layer of cortical bone of transverse process 323. In this case, the warning signal exceeds second critical threshold SC2, representative of breaching the cortical bone, before fourth depth threshold SP4 is attained. Control unit 111, which may impose a reduced advancement speed when first critical threshold SC1 identifying the interface C" between cancellous bone and cortical bone is detected, imposes a zero speed at second critical threshold SC2.

Figure 13:
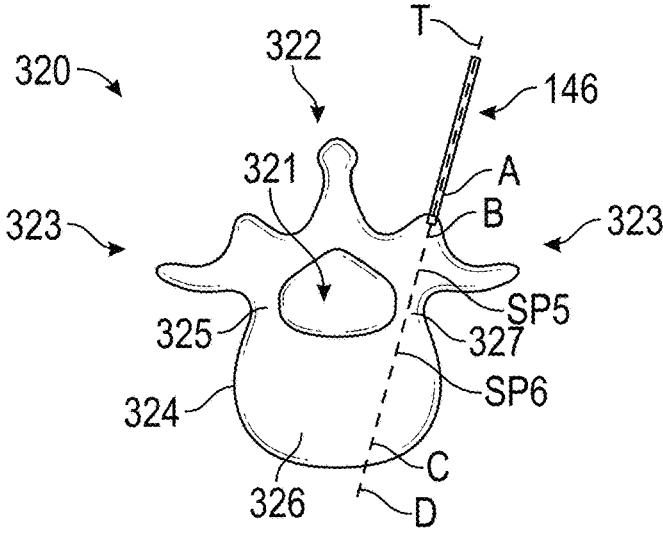
Figure 13:
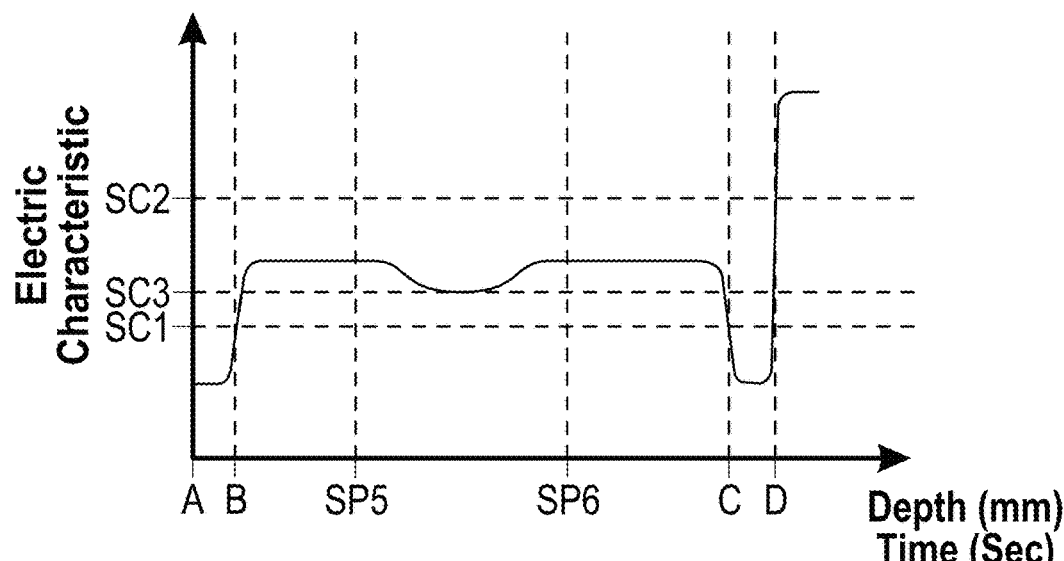
Figure 13:
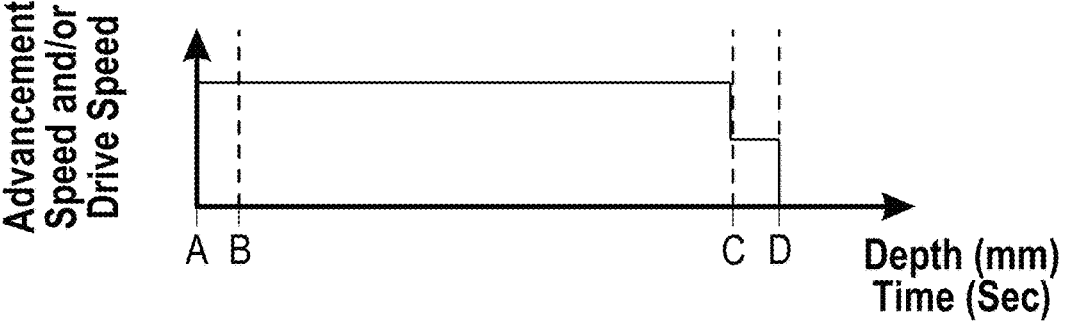

FIG. 13 depicts the signature for tip 147 of drill bit 146 entering pedicle 327 where the density of the cancellous bone increases, leading to a reduction in conductivity. This reduction may be identified by third critical threshold SC3, for example defined in a differential manner, meaning by a variation of the measurement parameter, within a defined spatial window between fifth SP5 and sixth SP6 depth thresholds. Within this spatial window, the warning signal must not exceed second critical threshold SC2, representative of a breach resulting from reaching one among inner layer 325 and outer layer 324 of cortical bone. Upon passage through pedicle 323, the drive speed of drill bit 146 may, for example, increase.

Figure 14:
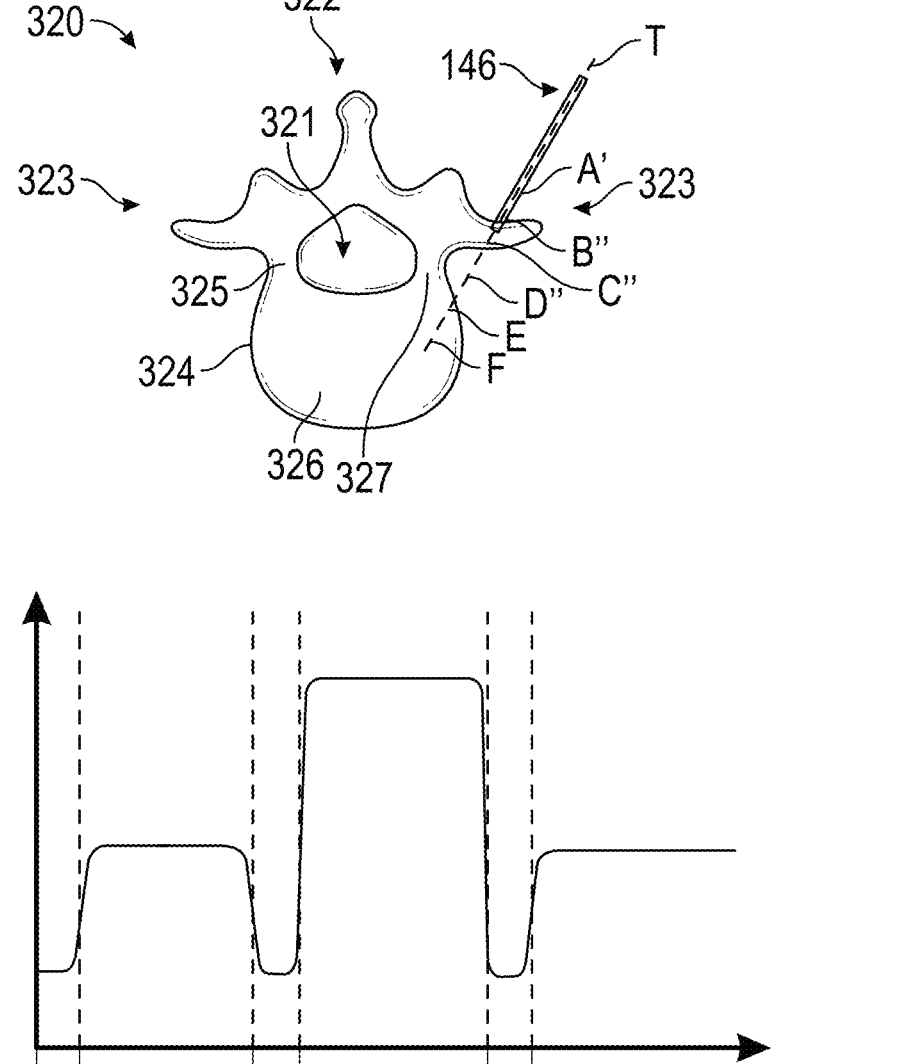

FIG. 14 depicts the signature corresponding to traversing one of transverse processes 323 followed by a new penetration into outer layer 324 of cortical bone. Although represented in the figures as a function of depth, variations in the measurement parameter also could be obtained as a function of time.

In accordance with a yet further aspect of the invention, precision guidance system 102 also may include a force measurement device connected to control unit 111 that is configured to emit a force signal corresponding to a force exerted on drill bit 146. In this embodiment, the force exerted on drill bit 146 may comprise one or more forces in all relevant directions, one or more torques in all relevant directions, or a combination thereof. The force measurement device may be of any suitable type, for example, including one or more force sensors integrated into robot 108 that enable determination of the force on drill bit 146 based on the forces and/or torques exerted by the actuators.

In the foregoing embodiment, control unit 111 may control the movement of drill bit 146 as a function of the force signal in addition to controlling it as a function of the warning signal, and if necessary, of the depth signal. In particular, control unit 111 may allow movement of drill bit 146 in the advancement direction as long as the force signal has not reached a force threshold SF, and may modify movement of drill bit 146 when the force signal reaches force threshold SF. A reference force signal resulting from a variation of a force parameter related to the force exerted on drill bit 146 during penetration of the drill bit into the reference anatomical portion may be provided in each signature and combined with the reference warning signal, and where appropriate with the reference depth signal.

Figure 15:
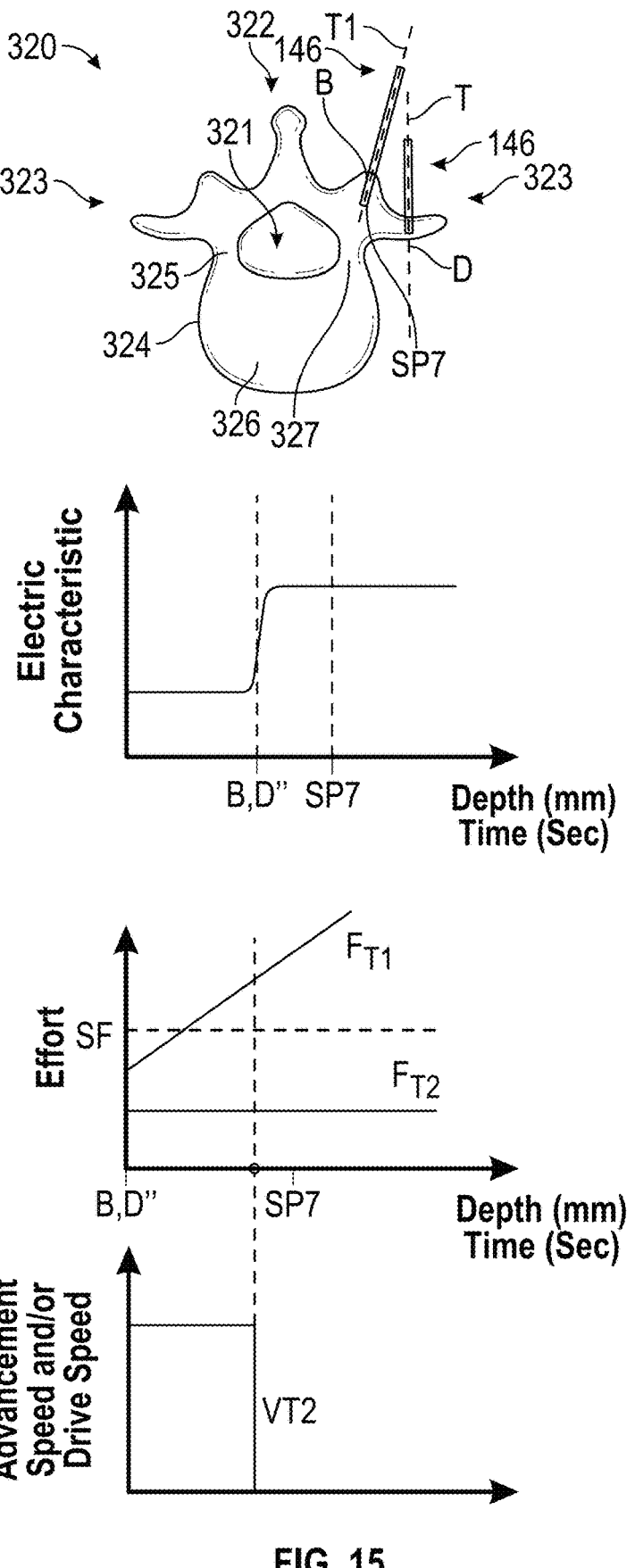

FIG. 15 depicts operation of a system that combines warning and force signals to differentiate between two different positions of drill bit 146. In first penetration direction T1, drill bit 146 exits outer layer 324 of cortical bone at exit point B facing pedicle 327. In second penetration direction T2, drill bit 146 exits outer layer 324 of cortical bone at exit point D" in one of the transverse processes 323. Traversing the outer layer of cortical bone to reach cancellous bone in first penetration direction T1 and traversing the outer layer of cortical bone to reach soft tissue in the second penetration direction may result in similar warning signals being issued. By contrast, cancellous bone, which has greater hardness than soft tissue, will result in an increase in the force signal that may be characterized by exceeding a defined force threshold SF. Under such conditions, when the warning signal increases due to a passage from cortical bone to either cancellous bone or soft tissue, the force signal may be monitored. If force signal FT2 does not exceed force threshold SF after reaching depth threshold SP7, for example equal to 5 mm, control unit 111 detects the position of drill bit 146 in second direction T2 and modifies the movement, for example by reducing the speed of drill bit 146 to zero at VT2. Such differentiation may be obtained for tissues other than cancellous bone and soft tissue. The force signal may, for example, be used to differentiate between cortical bone and a fatty cyst having similar electrical conductivities.

EXAMPLE

Robot 108 is a Barrett WAM arm with 7 degrees of freedom, and is naturally reversible, allowing it to be manipulated by hand to easily be placed in a desired configuration. Robot 108 is controlled by control unit 111 consisting of a control PC using the proprietary libbarrett API based on the Xenomai real-time system.

The software interface with drilling device 112 is achieved via a tinyTILE board integrating a Bluetooth-compatible microcontroller; the board communicates with the control PC via a virtual USB serial port.

Drill bit 146 is driven by the drive device comprising a gear motor unit fixed to effector end 132 of robotic arm 134. The unit includes a Maxon EC45 Flat motor (ref. 350910) and a 50:1 SGP67S 50 reduction gear. Its characteristics are as follows:

Rated speed under load: 78 rpm

Rated torque: 2.80 Nm

Rated current: 3 A

Robot 108 is controlled to enable:

1. Positioning of the instrument by the surgeon "by hand", before insertion (co-manipulated mode)

2. Automatic insertion of the instrument, by means of a feedback loop (negative feedback) for the measurement of tissue conductivity in real time by drilling device 112.

The operation performed is as follows. Before manipulation, drill bit 146 is mounted on a drill mounted in advance on robotic arm 134 and whose speed can be regulated. The surgeon is positioned next to the vertebra and robotic arm 134. The robotic arm is in "locked" mode, holding drilling device 112 in place.

For the manipulation, the surgeon takes hold of drilling device 112 and presses on a pedal to "unlock" robotic arm 134. He then may freely change the position and orientation of drill bit 146 by co-manipulation. The surgeon places the instrument in the "ready to drill" position (alignment along the penetration direction, in contact with the entry point) and may check the orientation and trajectory using monitor 106. When the position is correct, he releases the pedal and robotic arm 134 returns to locked mode. If necessary, adjustments may be made to the point of entry and penetration direction, with changes in trajectory being visualized on monitor 106.

Via the interface (possibly with an operator), the surgeon triggers insertion in automatic mode. The drive mechanism is started at drive speed $\omega_1$ (for example 300 rpm). The robot advances in the advancement direction along the penetration direction at advancement speed v1 (for example 1 mm/s) and begins monitoring the warning signal.

During the first 5 mm, the value of the warning signal may decrease to reach a stable value, called the reference value. Control unit 111 identifies this reference online because it can vary from one patient to another. The control unit continuously monitors the warning signal and orders advancement as long as the warning signal is close to the reference and the variation in the warning signal is "fairly slow". When these conditions are no longer met: the robotic arm is stopped and the drive speed ($\omega_2$ (for example 100 rpm) are ordered.

The position is saved and piercing of the cortical bone is initiated. The cortical bone is pierced, for example at an advancement speed v2 of 0.2 mm/s, until a breach is detected which causes stopping of robot 108 and drill bit 146. The drilling device is withdrawn from the vertebra.

Instrumentation and Control

Two controllers have been developed.

During the manual placement and repositioning phases, robotic arm 134 only compensates for its own weight. It is therefore freely movable by hand due to the high reversibility of its cable transmission system. For the drilling, a specific control schematic has been developed. The feedback-control schematic takes a desired orientation, a desired initial position, and an advancement speed as input. The operating modes it implements are as follows.

At startup, the position $X_{ini}$ and the orientation $\downarrow_{ini}$ of the robot are saved. The desired positions and orientations are initialized (respectively $X_{des}\leftarrow X_{ini}$ and $\theta_{des}\leftarrow\theta_{ini}$). As long as the force applied by robotic arm 134 to the vertebra (force estimated via the motor currents and a kinematic model of the robot) is below a threshold value F, the desired position is incremented, as follows:

$$X_{des} \leftarrow X_{des} + V_{des}\Delta T$$

$V_{des}$ being the advancement speed of the drilling defined by the user (vector oriented along the axis of the drilling), and $\Delta T$ being the cycle time of the robot controller (2 ms).

The controller then calculates a force to be applied via a proportional derivative corrector:

$$F \leftarrow K_{pp}(X_{des} - X) - K_{dp}V$$

where $K_{pp}$ and $K_{dp}$ are the proportional and derivative gains in position, respectively. This force then is compared to $F_{max}$ and saturated if it exceeds this value.

Finally, the joints' torques for verifying the position are calculated via the robot's static transmission model:

$$\tau_p \leftarrow (J^T)_{13}F$$

where $(J^T)_{13}$ represents the first three columns of the transpose of the robot's natural Jacobian matrix.

The orientation is controlled with an independent PD corrector calculating the moment M:

$$M \leftarrow K_{po} \in \theta - K_{do}(l)$$
$$\tau_\theta \leftarrow (J^T)_{46}M$$

where $K_{po}$ and $K_{do}$ respectively are the proportional and derivative gains in orientation, $\in_\theta$ is the error in orientation, $\omega$ is the rotation speed, and $(J^T)_{46}$ represents the first three columns of the transpose of the natural Jacobian matrix of the robot.

The gains are adjusted to obtain an appropriate stiffness (keeping the drill aligned) and good damping, by trial and error. Adjusted gain values:

Orientation controller: $K_{po}$=18 and $K_{do}$=0.087
Position controller: $K_{pp}$=5000 and $K_p$=60
When drilling begins, the advancement speed is requested from the robot.

Contact between the instrument and bone produces a resistive force. This force creates a monitoring error. As the speeds are low, we can estimate that:

$$F = K_{pp}(X_{des} - X) - K_{dp}V - K_{pp}(X_{des} - X)$$

Therefore the error is proportional to the force applied. The desired position thus is located in front of the tip and the proportional corrector is comparable to a spring which "pulls" the instrument. When the resistive force becomes large, this corresponds to a large error: there is no point in continuing to advance the desired position at full speed, which is why the force is saturated.

The warning signal measured by drill bit 146 is filtered before being sent via Bluetooth. This filter is in the form:

$$\sigma(t) = \alpha s(t) + (1 - \alpha)\sigma(l - T)$$

where a=⅓, s(t) being the unprocessed signal measured at time t, $\sigma(t)$ the value of the filtered signal at time t, and T the acquisition period (around 200 ms).

The goal is to stop the robot's progress when rapid variations in the signal are observed, and a delay of more than one second may cause a breach at the end of drilling. We therefore integrate an algorithm into the robot control during signal preprocessing, which reverses the filter:

$$s(t) = \frac{\sigma(t) - (1 - \alpha)\sigma(t - 1)}{\alpha}$$

This makes it possible to recover the unprocessed value of the signal at time t from the filtered signal, and at the same time to cancel out the delays.

The warning signal is used to stop the robotic arm just before a breach is made. The algorithm used is as follows.

Penetration into the cortical bone is detected when the warning signal drops below a critical threshold $sc_1$. When the cortical bone has been penetrated, an impending breach is detected when the signal rises above its minimum value $s_{min}$ with a deviation greater than a threshold $sc_2$.

In the experiments conducted, the thresholds $sc_1$ and $sc_2$ are imposed before the experiment (adjustment made based on initial tests). By contrast, the minimum reference value $s_{min}$ is not very repeatable from one drilling to another; it is therefore calculated automatically online.

The interpretation of the instrument signal can be described by the following pseudo-code:

Initialization: $s_{min}\leftarrow\infty$; flag$_{cortical}$=0
For each new value received from the signal (t), loop as follows:
1. Calculate the Minimum Signal Value:
   If s(t)<$S_{min}$, then $S_{min}\leftarrow$s(t)
2. Detect Entry into the Cortical Bone:
   If s(t)<$S_1$ and flag$_{cortical}$=0, then flag$_{cortical}\leftarrow$1
3. in the Cortical Bone, Detect an Impending Breach:
   If flag$_{cortical}$=1 and (s(t)-$s_{min}$)>$s_2$, then stop drilling.
   The thresholds were set to: $S_1$=0.15 V and $S_2$=0.3 V.

During drilling, the rotation speed of the motor is not explicitly controlled: the motor is sent a command equal to 24 Volts which corresponds to an idle speed of the motor of about 80 revolutions per minute. This command remains in an open loop throughout the drilling. It should be noted that when the drill bit has penetrated deeply, resistance is strong and the rotation speed decreases. One of the advantages of reducing the axial force is that it also (mechanically) reduces the opposing torque to the drilling, which makes it possible to prevent the drill bit from jamming.

Initiating the drilling therefore simply amounts to setting a positive advancement speed. Stop the supply of electricity to the motor for rotating the drill bit. Assign the desired position of the robot to the current position, which has the effect of immediately stopping the application of force. A withdrawal of robotic arm 134 may then be observed.

What is claimed is:

1. A surgical system for executing a surgical plan of penetrating an anatomical portion, the surgical system for use in conjunction with an imaging system, the surgical system comprising:

a surgical tool having a cutting tip configured to penetrate the anatomical portion and a sensor to measure an electrical characteristic of the anatomical portion;

a guidance system coupled to the imaging system and the surgical tool, wherein the guidance system is configured to:

receive the surgical plan, the surgical plan identifying a specified orientation, trajectory and depth for penetration of the anatomical portion;

receive and display images from the imaging system of the anatomical portion;

receive sensor data from the sensor during penetration of the anatomical portion, wherein the sensor data corresponds to an electrical characteristic of the anatomical portion;

determine whether the sensor data corresponds to the surgical plan; and display an indication of the orientation, trajectory and depth of the surgical tool as an overlay on the images of the anatomical portion, wherein the guidance system further is configured to continuously update the overlay of the indication of the orientation, trajectory and depth of the surgical tool on the display and to adjust real-time registration of the indication of the orientation, trajectory and depth of the surgical tool in the overlay responsive to the sensor data.

2. The surgical system of claim 1, wherein the surgical tool is a drill bit and the sensor comprises first and second electrodes disposed on the drill bit.

3. The surgical system of claim 2, wherein the sensor is configured to measure electrical impedance of the anatomical portion in contact with the cutting tip.

4. The surgical system of claim 1, wherein the indication of the orientation, trajectory and depth of the surgical tool comprises corresponds to a transition between any of cortical bone and cancellous bone, cortical bone and soft tissue or blood, or cancellous bone and soft tissue or blood.

5. The surgical system of claim 4, wherein adjusting registration of the indication of the orientation, trajectory and depth of the surgical tool in the overlay comprises adjusting a position of the transition in the overlay and images of the anatomical portion.

6. The surgical system of claim 5, wherein the guidance system further is configured to generate an alert in response to a determination that the sensor data does not correspond to the surgical plan.

7. The surgical system of claim 6, wherein the alert comprises an audible sound.

8. The surgical system of claim 1, wherein the guidance system further is configured, in response to a determination that the sensor data does not correspond to the surgical plan, to propose a revised trajectory, orientation or depth of the surgical tool in the overlay to restore compliance with surgical plan.

9. The surgical system of claim 1, wherein the guidance system further is configured to store a plurality of predefined signatures, each predefined signature comprising a variation in the electrical characteristics expected to be encountered during execution of the surgical plan.

10. The surgical system of claim 9, wherein the guidance system further is configured, during penetration of the surgical tool into the anatomical portion, to continuously compare the sensor data to at least one of the plurality of predefined signatures.

11. A surgical system for use with an imaging system, the surgical system comprising:

a surgical tool having a sensor to measure electrical characteristics of an anatomical portion;

a guidance system coupled to the imaging system and the surgical tool, wherein the guidance system is configured to:

receive a surgical plan that identifies a specified orientation, trajectory and depth for penetration of the anatomical portion, the surgical plan including a variation in an expected electrical characteristic of the anatomical portion to be encountered during execution of the surgical plan;

receive from the imaging system and display real-time images of the anatomical portion;

receive sensor data from the sensor during penetration of the anatomical portion, the sensor data corresponding to a measured electrical characteristic of the anatomical portion;

determine whether the sensor data corresponds to the surgical plan by comparing the measured electrical characteristic to the expected electrical characteristic; and display an indication of the orientation, trajectory and depth of the surgical tool as an overlay on the images of the anatomical portion, wherein the guidance system further is configured to continuously update the overlay of the indication of the orientation, trajectory and depth of the surgical tool on the display and to adjust real-time registration of the indication of the orientation, trajectory and depth of the surgical tool in the overlay responsive to the sensor data.

12. The surgical system of claim 11, wherein the surgical tool is a drill bit having a cutting tip and the sensor comprises first and second electrodes disposed on the drill bit.

13. The surgical system of claim 12, wherein the sensor is configured to measure electrical impedance of the anatomical portion in contact with the cutting tip.

14. The surgical system of claim 12, wherein the variation in the expected electrical characteristic of the anatomical portion corresponds to a transition of electrical characteristic between any of cortical bone and cancellous bone, cortical bone and soft tissue or blood, or cancellous bone and soft tissue or blood.

15. The surgical system of claim 14, wherein adjusting registration of the indication of the orientation, trajectory and depth of the surgical tool in the overlay comprises adjusting a position of the transition in the overlay and images.

16. The surgical system of claim 11, wherein the guidance system further is configured to generate an alert in response to a determination that the sensor data does not correspond to the surgical plan.

17. The surgical system of claim 16, wherein the alert comprises an audible tone.

18. The surgical system of claim 11, wherein the guidance system further is configured to propose a revised trajectory, orientation or depth of the surgical tool in the overlay to restore compliance with surgical plan.

19. The surgical system of claim 11, wherein the guidance system further is configured to store a plurality of predefined signatures, each predefined signature corresponding to a variation in the electrical characteristics expected to be encountered during execution of the surgical plan.

20. The surgical system of claim 19, wherein the guidance system further is configured, during penetration of the surgical tool into the anatomical portion, to continuously compare sensor data to at least one of the plurality of predefined signatures.

\* \* \* \* \*